US008917920B2

(12) United States Patent
Matsuda et al.

(10) Patent No.: US 8,917,920 B2
(45) Date of Patent: Dec. 23, 2014

(54) IMAGE PROCESSING APPARATUS, IMAGE PROCESSING METHOD, AND COMPUTER PROGRAM PRODUCT

(71) Applicant: Olympus Corporation, Tokyo (JP)

(72) Inventors: Takehiro Matsuda, Hachioji (JP); Yamato Kanda, Hino (JP)

(73) Assignee: Olympus Corporation, Tokyo (JP)

(*) Notice: Subject to any disclaimer, the term of this patent is extended or adjusted under 35 U.S.C. 154(b) by 0 days.

(21) Appl. No.: 14/061,378

(22) Filed: Oct. 23, 2013

(65) Prior Publication Data

US 2014/0044328 A1 Feb. 13, 2014

Related U.S. Application Data

(60) Division of application No. 12/421,715, filed on Apr. 10, 2009, now Pat. No. 8,594,396, which is a continuation of application No. PCT/JP2007/068565, filed on Sep. 25, 2007.

(30) Foreign Application Priority Data

Oct. 11, 2006 (JP) ................. 2006-278038

(51) Int. Cl.
*G06T 7/00* (2006.01)
*A61B 1/04* (2006.01)

(52) U.S. Cl.
CPC ............. *G06T 7/0014* (2013.01); *G06T 7/0012* (2013.01); *A61B 1/04* (2013.01); *G06T 2207/30004* (2013.01)
USPC .......................................... 382/128

(58) Field of Classification Search
CPC ................. G06T 7/0012; G06T 2207/30004; A61B 1/04
See application file for complete search history.

(56) References Cited

U.S. PATENT DOCUMENTS 5,311,328 A 5/1994 Murata
7,907,775 B2 3/2011 Inoue et al.
(Continued)

FOREIGN PATENT DOCUMENTS

EP 1 875 855 A1 1/2008
JP H6-503483 4/1994
(Continued)

OTHER PUBLICATIONS

European Supplementary Search Report dated Oct. 28, 2011 from corresponding European Application No. EP 07 807 837.5.
B.V. Dhandra, Ravindra Hegadi, Mallikarjun Hangarge, V. S. Malemath, "Analysis of Abnormality in Endoscopic images using Combined HSI Color Space and Watershed Segmentation," icpr, vol. 4, pp. 695-698, 18th International Conference on Pattern Recognition (ICPR'06) vol. 4, 2006.

(Continued)

*Primary Examiner* — Marcos D. Pizarro
*Assistant Examiner* — Sue Tang
(74) *Attorney, Agent, or Firm* — Scully, Scott, Murphy & Presser, P.C.

(57) ABSTRACT

An image processing apparatus for performing an image processing on a body cavity image captured in a living body includes: a storage unit which stores information including image information of the body cavity image; a change amount calculator which reads out the image information of the body cavity image from the storage unit and calculates, in the read body cavity image, a pixel value change amount of a pixel of interest with a plurality of surrounding pixels located around the pixel of interest; and a candidate lesion region detector which detects a candidate lesion region in the body cavity image based on a calculation result of the change amount calculator.

7 Claims, 18 Drawing Sheets

(56) References Cited

U.S. PATENT DOCUMENTS

| | | | |
|---|---|---|---|
| 2004/0258285 A1* | 12/2004 | Hansen et al. | 382/128 |
| 2005/0053270 A1* | 3/2005 | Kasai et al. | 382/128 |
| 2005/0232483 A1 | 10/2005 | Kato et al. | |
| 2008/0205785 A1* | 8/2008 | Geiger et al. | 382/260 |

FOREIGN PATENT DOCUMENTS

| | | |
|---|---|---|
| JP | 2002-325762 | 11/2002 |
| JP | 2004-521693 | 7/2004 |
| JP | 2005-80758 | 3/2005 |
| JP | 2006-218138 | 8/2006 |
| JP | 2006-304993 | 11/2006 |
| WO | 91/19457 | 12/1991 |
| WO | 02/073507 A2 | 9/2002 |
| WO | 2005/101314 A2 | 10/2005 |

OTHER PUBLICATIONS

Canny, J., "A Computational Approach to Edge Detection", IEEE Transactions on Pattern Analysis and Machine Intelligence, vol. PAMI-8, No. 6, Nov. 1986, pp. 679-698.

Decision on Patent Grant dated Oct. 9, 2012 from related application JP 2006-278038.

United States Office Action dated Dec. 20, 2011 from related U.S. Appl. No. 12/421,715.

United States Office Action dated Jul. 17, 2012 from related U.S. Appl. No. 12/421,715.

United States Office Action dated Jan. 7, 2013 from related U.S. Appl. No. 12/421,715.

Notice of Allowance dated Jul. 24, 2013 from related U.S. Appl. No. 12/421,715.

\* cited by examiner

FIG.9

| $P_1$ | $P_2$ | $P_3$ |
|---|---|---|
| $P_4$ | IP | $P_5$ |
| $P_6$ | $P_7$ | $P_8$ |

FIG.10

| | $P_1$ | |
|---|---|---|
| $P_2$ | IP | $P_3$ |
| | $P_4$ | | ns
IMAGE PROCESSING APPARATUS, IMAGE PROCESSING METHOD, AND COMPUTER PROGRAM PRODUCT

CROSS-REFERENCE TO RELATED APPLICATIONS

This application is a divisional application of U.S. application Ser. No. 12/421,715 filed on Apr. 10, 2009, which claims the benefit of priority from Japanese Patent Application No. 2006-278038, filed on Oct. 11, 2006; and PCT International Application No. PCT/JP2007/068565, filed on Sep. 25, 2007, all of which are hereby incorporated by reference into the present application.

BACKGROUND OF THE INVENTION

1. Field of the Invention

The present invention relates to an image processing apparatus which detects a lesion in a body cavity image (or digestive organ image) captured in an inside of a living body, an image processing method, and a computer program product.

2. Description of the Related Art

Conventionally, as a processing of detecting a lesion with respect to a body cavity image captured in an inside of a living body, a technique of dividing the image into blocks, calculating color information of each block, and comparing a reference value for color information of a known lesion such as a bleeding site with a reference value for color information of a healthy tissue has been disclosed in Japanese translation No. 2004-521693 of PCT international application.

In addition, a technique of detecting a focal shadow (or calcification masses) with respect to a medical image has been known, for example, in Japanese Patent Application Laid-Open No. 2002-325762. In the technique presented herein, an image is scanned in sequence and an average of image values in a small region in which a pixel of interest is located in the center thereof is obtained for detecting a candidate focal shadow. A border of the candidate focal shadow is detected by categorizing each pixel in the small region into one of two groups depending on whether the pixel is larger or smaller than the average of the image values in the small region, obtaining an average of coordinate positions of pixels categorized into each one of the two groups, and extracting a place where a difference in distance among the coordinate positions is present. Thereafter, whether or not the region is a shadow caused by a focus is identified depending on a manner of a pixel value change in pixels lying between a pixel in the candidate focal shadow region and a pixel outside the region.

In Japanese Patent Application Laid-Open No. 2002-325762, a detection of a focal shadow by using the Quoit filter is disclosed as a conventional technique. The Quoit filter is formed by a circular filter and a ring filter surrounding the circular filter. When each pixel of an image is scanned by the Quoit filter, the circular filter shows a large value in a region where a luminance locally rises while the ring filter shows a small value. This enables a detection of a focus whose luminance is locally high.

SUMMARY OF THE INVENTION

According to an aspect of the present invention, an image processing apparatus for performing an image processing on a body cavity image captured in a living body, includes: a storage unit which stores information including image information of the body cavity image; a change amount calculator which reads out the image information of the body cavity image from the storage unit and calculates, in the read body cavity image, a pixel value change amount of a pixel of interest with a plurality of surrounding pixels located around the pixel of interest; and a candidate lesion region detector which detects a candidate lesion region in the body cavity image based on a calculation result of the change amount calculator.

According to another aspect of the present invention, an image processing method to be performed by a computer which is capable of performing an image processing on a body cavity image captured in a living body and includes a storage unit that stores information including image information of the body cavity image, includes: calculating, after reading out the image information of the body cavity image from the storage unit, a pixel value change amount of a pixel of interest with a plurality of surrounding pixels located around the pixel of interest with respect to the read body cavity image; and detecting a candidate lesion region in the body cavity image based on a result of the calculating of the pixel value change amount.

According to still another aspect of the present invention, a computer program product causes a computer to perform the method according to the present invention.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 9 shows adjacent eight pixels of the pixel of interest;

FIG. 10 shows adjacent four pixels of the pixel of interest;

DETAILED DESCRIPTION OF THE PREFERRED EMBODIMENTS

Exemplary embodiments of the present invention will be explained below with reference to the accompanying drawings.

Figure 1:
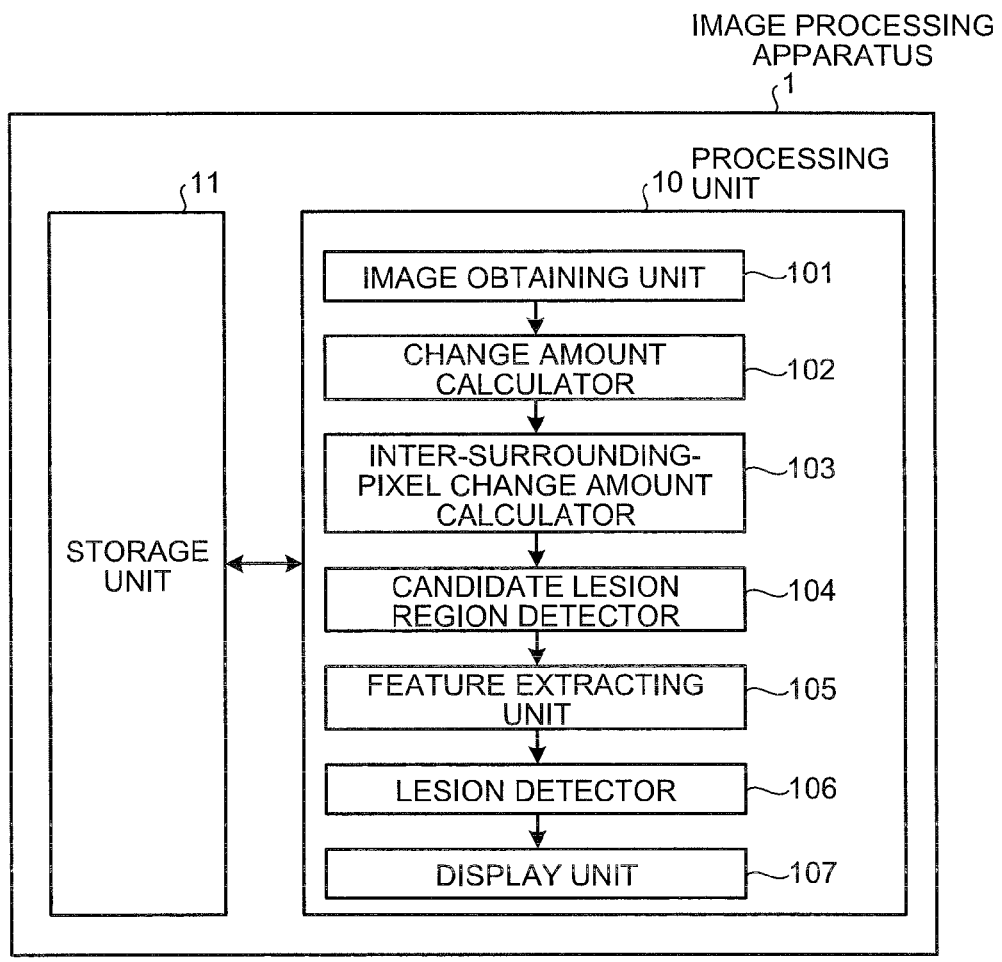
FIG. 1 is a block diagram of a configuration of an image processing apparatus according to a first embodiment of the present invention.

FIG. 1 is a block diagram of a configuration of an image processing apparatus according to a first embodiment of the present invention. An image processing apparatus 1 shown in FIG. 1, which performs an image processing on an image (a body cavity image) of an organ inside a living body to detect a lesion in the body cavity image, includes a processing unit 10 which performs a predetermined image processing and a storage unit 11 which stores image information of body cavity images and information to be used in the processing unit 10. The image processing apparatus 1 is constituted by a computer provided with a CPU, ROM, RAM, and the like.

The processing unit 10 includes: an image obtaining unit 101 which obtains a body cavity image of an organ inside the living body; a change amount calculator 102 which calculates a pixel value change amount between a pixel of interest and surrounding pixels; an inter-surrounding-pixel change amount calculator 103 which calculates a pixel value change amount between the surrounding pixels; a candidate lesion region detector 104 which detects a candidate lesion region in the body cavity image based on the calculation result by the change amount calculator 102 and the calculation result by the inter-surrounding-pixel change amount calculator 103; a feature extracting unit 105 which extracts a feature of the candidate lesion region detected by the candidate lesion region detector 104; a lesion detector 106 which detects a lesion region based on the result extracted by the feature extracting unit 105; and a display unit 107 which displays the lesion detected by the lesion detector 106.

Figure 2:
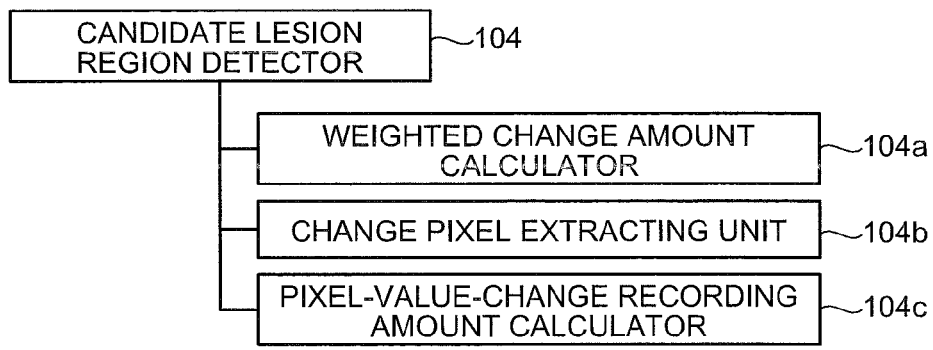
FIG. 2 is a block diagram of a configuration of a candidate lesion region detector.

As shown in FIG. 2, the candidate lesion region detector 104 includes a weighted change amount calculator 104a which calculates a weighted pixel value change amount by using the pixel value change amount, calculated by the change amount calculator 102, with the surrounding pixels and the pixel value change amount, calculated by the inter-surrounding-pixel change amount calculator 103, between the surrounding pixels and giving a weighting according to a balance degree of the surrounding pixels; a change pixel extracting unit 104b which, when the weighted pixel value change amount calculated by the weighted change amount calculator 104a exceeds a predetermined threshold value in predetermined all directions from the pixel of interest as a center, extracts the pixel of interest as a pixel value change pixel; and a pixel-value-change recording amount calculator 104c which calculates, with respect to the pixel value change pixel in the image, a pixel-value-change recording amount as a pixel value change amount to be recorded to the pixel of interest by using the weighted pixel value change amount calculated for each of the predetermined directions from the pixel of interest as the center.

The CPU of the image processing apparatus 1 with the above-described configuration reads out an image processing program for executing an image processing method (to be described later) according to the first embodiment from the storage unit 11 to execute a calculation processing related to the image processing method.

Figure 3:
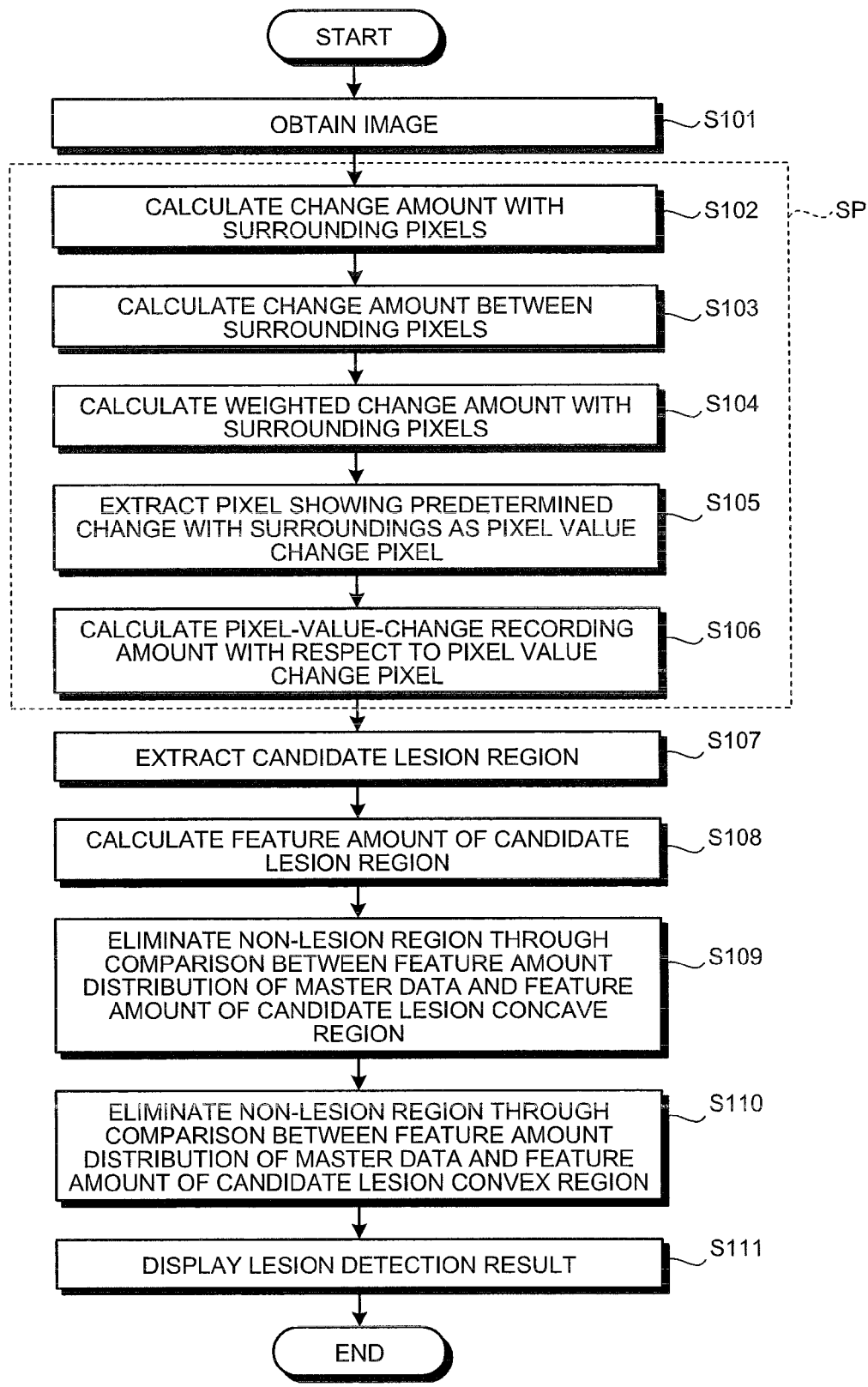
FIG. 3 is a flowchart of a summary of an image processing method according to the first embodiment of the present invention.

FIG. 3 is a flowchart of a summary of a processing in the image processing method performed by the image processing apparatus 1. The summary of the processing in the image processing method according to the first embodiment will be explained below with reference to FIG. 3.

First, the image obtaining unit 101 obtains the image captured inside the body cavity (the body cavity image) from the storage unit 11 (step S101).

Figure 4:
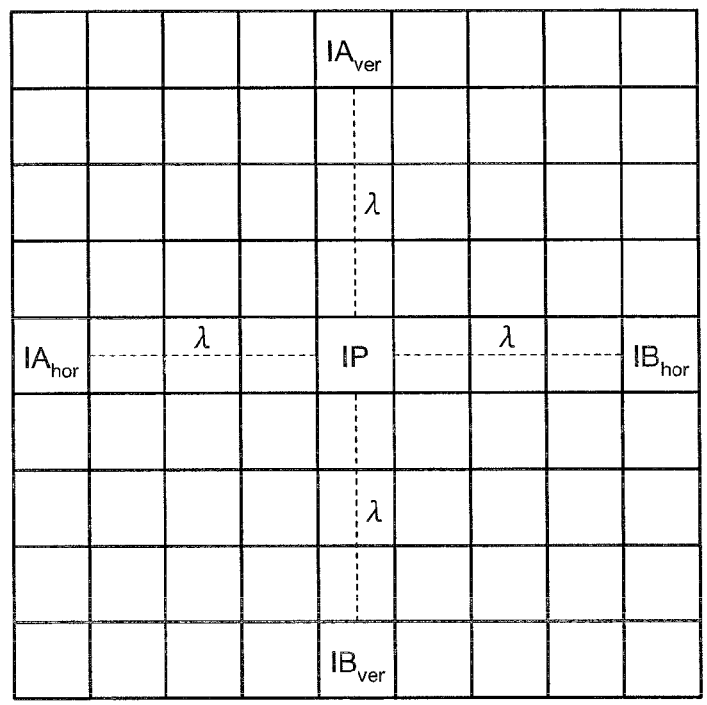
FIG. 4 shows an example (first example) of setting surrounding pixels with respect to a pixel of interest.
Figure 5:
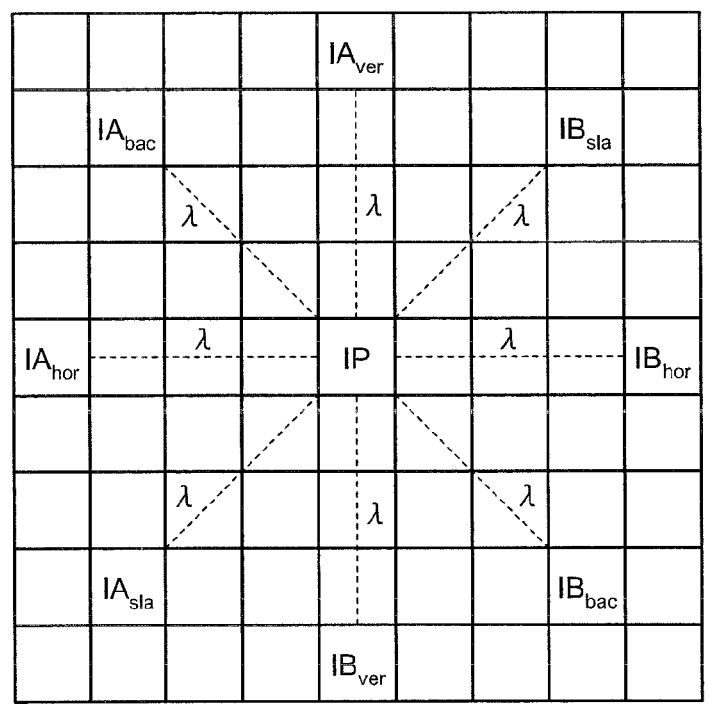
FIG. 5 shows an example (second example) of setting surrounding pixels with respect to a pixel of interest.

Then as shown in FIGS. 4 and 5, the change amount calculator 102 calculates a pixel value change amount by using surrounding pixels $IA_{dir}$ and $IB_{dir}$ which are present a predetermined number of pixels λ (or a distance corresponding to the number of pixels λ) away from and around a pixel of interest IP as a processing target (step S102). Here, a suffix "dir" in the surrounding pixels shows a predetermined direction from the pixel of interest IP as a center and a specific direction will be explained later. The direction of the surrounding pixels may be set in advance and may be set each time by being input via a given input unit (not shown) by a user.

A candidate lesion region is generally considered to be present in a body cavity image as a part which shows a change in a pixel value from a pixel constituting a healthy tissue present around. Such a pixel value change tends to be present in a pixel having a color component corresponding to an absorption spectrum of blood. To take one example, when the body cavity image is an RGB image, a pixel value change due to a lesion tends to be present in the G channel. Therefore, the first embodiment is assumed to deal with a case of obtaining the RGB image at step S101 and to perform the pixel value change amount calculation in a G channel image of the RGB image. By calculating the pixel value change amount in this way, a lesion can be detected accurately and more favorably a high-speed of the processing can be realized.

A specific example of the pixel value change amount calculation with the surrounding pixels at step S102 will be explained. FIG. 4 shows an example of setting the pixel of interest IP and the surrounding pixels $IA_{dir}$ and $IB_{dir}$ in a case of calculating a pixel value change (concave/convex) amount with the surrounding pixels in two directions, i.e., the horizontal direction and the vertical direction. In FIG. 4, surrounding pixels present at symmetric positions the predetermined number of pixels λ away in the horizontal direction with respect to the pixel of interest IP are set to be $IA_{hor}$ and $IB_{hor}$, and surrounding pixels present at symmetric positions the predetermined number of pixels λ away in the vertical direction are set to be $IA_{ver}$ and $IB_{ver}$. First, a pixel value change amount $V_{hor}$ with the surrounding pixels in the horizontal direction is calculated by the following equation (1).

$$V_{hor} = IP - IM_{hor} \text{ where } IM_{hor} = \frac{IA_{hor} + IB_{hor}}{2} \quad (1)$$

Besides, a pixel value change amount $V_{ver}$ with the surrounding pixels in the vertical direction is calculated by the following equation (2).

$$V_{ver} = IP - IM_{ver} \quad (2)$$

where $$IM_{ver} = \frac{IA_{ver} + IB_{ver}}{2}$$

In the case of calculating the pixel value change amount with the surrounding pixels in each of the two directions, i.e., the horizontal and the vertical directions, two suffixes "hor" and "ver" correspond to the suffix "dir" described above.

Next, a case of obtaining a pixel value change with surrounding pixels in four directions at step S102 will be explained. FIG. 5 shows the pixel of interest IP and the surrounding pixels $IA_{dir}$ and $IB_{dir}$ in a case of calculating a pixel value change (concave/convex) amount with the surrounding pixels in four directions, i.e., the horizontal direction, the vertical direction, a diagonally-right-up direction, and a diagonally-right-down direction. In the case shown in FIG. 5, a pixel value change amount $V_{sla}$ with the surrounding pixels in the diagonally-right-up direction and a pixel value change amount $V_{bac}$ with the surrounding pixels in the diagonally-right-down direction are calculated, in addition to the pixel value change amount $V_{hor}$, calculated by equation (1), with the surrounding pixels in the horizontal direction and the pixel value change amount $V_{ver}$, calculated by equation (2), with the surrounding pixels in the vertical direction. Of the additional two directions, the pixel value change amount $V_{sla}$ with the surrounding pixels in the diagonally-right-up direction is calculated by the following equation (3).

$$V_{sla} = IP - IM_{sla} \quad (3)$$

where $$IM_{sla} = \frac{IA_{sla} + IB_{sla}}{2}$$

Besides, the pixel value change amount $V_{bac}$ with the surrounding pixels in the diagonally-right-down direction is calculated by the following equation (4).

$$V_{bac} = IP - IM_{bac} \quad (4)$$

where $$IM_{bac} = \frac{IA_{bac} + IB_{bac}}{2}$$

In the case of calculating the pixel value change amount with the surrounding pixels in each of the four directions, i.e., the horizontal direction, the vertical direction, the diagonally-right-up direction, and the diagonally-right-down direction, four suffixes "hor", "ver", "sla", and "bac" correspond to the suffix "dir" described above.

Figure 6A:
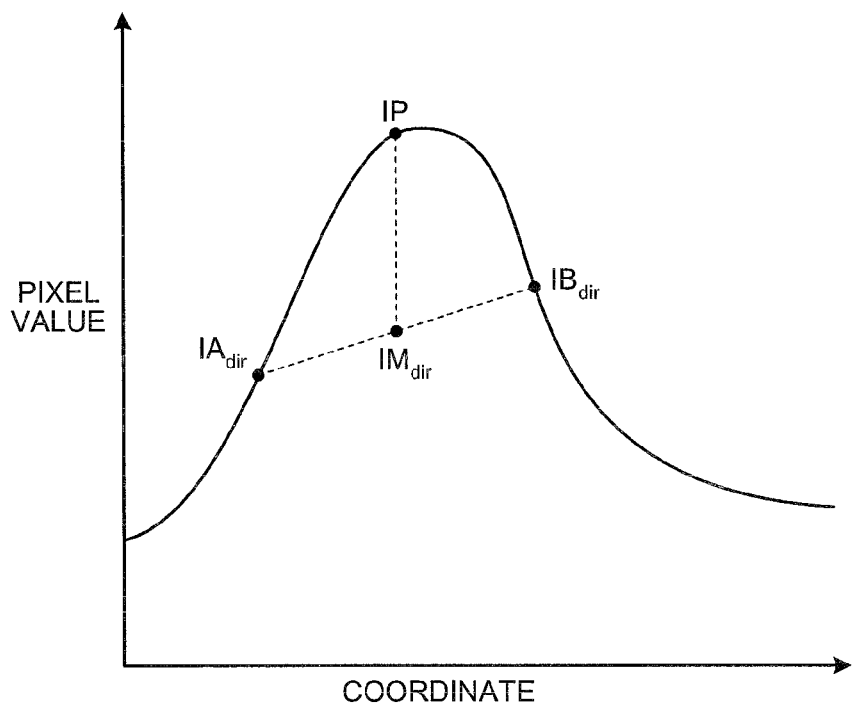
FIG. 6A shows a summary (when a change shows a convex) of calculating a pixel value change amount.
Figure 6B:
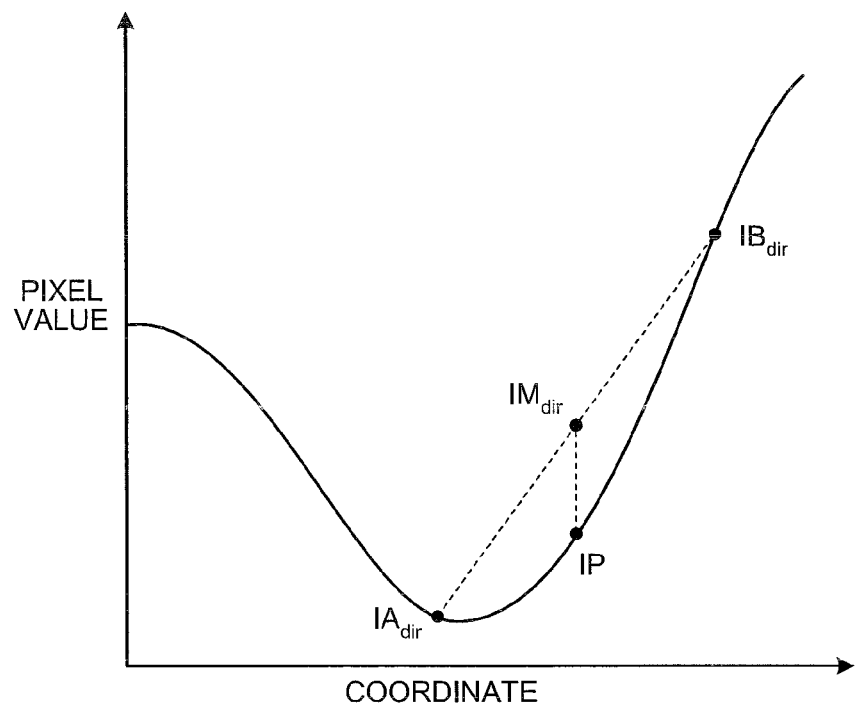
FIG. 6B shows a summary (when a change shows a concave) of calculating a pixel value change amount.

FIGS. 6A and 6B show a summary of the pixel value change amount calculation with the surrounding pixels in a given direction (the given direction being treated as "dir") at step S102. Of the two, when a change of the pixel of interest IP from the surrounding pixels $IA_{dir}$ and $IB_{dir}$ shows a convex as shown in FIG. 6A, the pixel value change amount $V_{dir}$ with the surrounding pixels becomes a positive value. In contrast, when the change of the pixel of interest IP from the surrounding pixels $IA_{dir}$ and $IB_{dir}$ shows a concave as shown in FIG. 6B, the pixel value change amount $V_{dir}$ with the surrounding pixels becomes a negative value.

Figure 7:
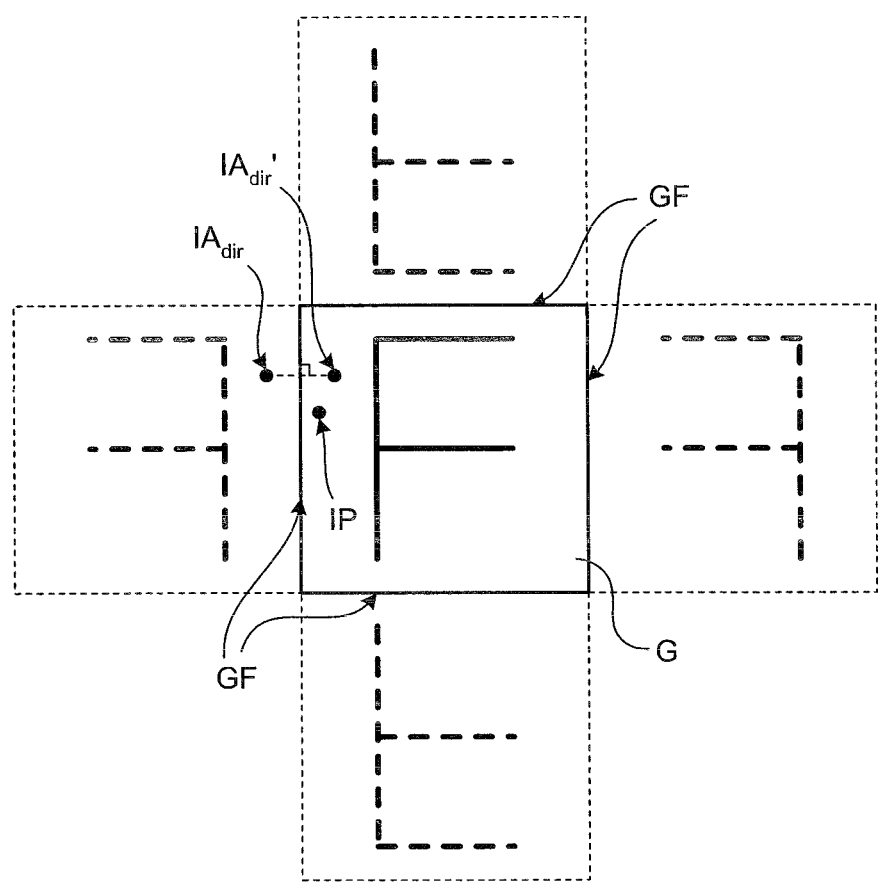
FIG. 7 shows a summary of calculating a pixel value change amount when a surrounding pixel gets out of an image range.

Here, a method of calculating the pixel value change amount with the surrounding pixels in a case where the pixel of interest IP is located at a margin of the image and any of the surrounding pixels gets out of a range of the image will be explained with reference to FIG. 7. When the surrounding pixel $IA_{dir}$ as a target for calculating the change amount with respect to the pixel of interest IP gets out of a range of an image G as shown in FIG. 7, a pixel $IA_{dir}'$ which is obtained inside the image G by folding back to a line-symmetric position from a border frame GF, as a symmetric axis, of the image G, is regarded as a surrounding pixel as the target for calculating the change amount. It should be noted the folding when any surrounding pixel gets out of the range of the image G is not limited to the method described above, and may be done to a point-symmetric position from a crossing point, as a point of the symmetry, of the border frame GF and a line connecting the pixel of interest IP and the surrounding pixel. Moreover, though the explanation about the surrounding pixel $IA_{dir}$ with respect to the pixel of interest IP is made in FIG. 7, it is only necessary, also when the surrounding pixel $IB_{dir}$ gets out of the range of the image G, that a pixel $IB_{dir}'$ to be regarded as a surrounding pixel as the target for calculating the change amount is obtained similarly through the folding described above.

After step S102 explained above, the inter-surrounding-pixel change amount calculator 103 calculates the change amount of the surrounding pixels $IA_{dir}$ and $IB_{dir}$ opposite each other across the pixel of interest IP (step S103). First, in the case of calculating the pixel value change amount with the surrounding pixels in each of the two directions, i.e., the horizontal and the vertical directions as shown in FIG. 4, the pixel value change amount between the surrounding pixels is calculated in each of the horizontal and the vertical directions. Specifically, a surrounding pixel change amount $B_{hor}$ in the horizontal direction and a surrounding pixel change amount $B_{ver}$ in the vertical direction are calculated respectively by the following equations (5) and (6).

$$B_{hor} = \left\{1 - \left|\frac{IA_{hor} - IB_{hor}}{IMG\_MAX}\right|\right\}^2 \quad (5)$$

$$B_{ver} = \left\{1 - \left|\frac{IA_{ver} - IB_{ver}}{IMG\_MAX}\right|\right\}^2 \quad (6)$$

Here, the "IMG_MAX" represents a maximum value in a format of a target image.

On the other hand, in the case of calculating the pixel value amount with the surrounding pixels in each of the four directions, i.e., the horizontal direction, the vertical direction, the diagonally-right-up direction, and the diagonally-right-down direction as shown in FIG. 5, the pixel value change amount between the surrounding pixels is also calculated in each of the horizontal direction, the vertical direction, the diagonally-right-up direction, and the diagonally-right-down direction.

Specifically, in addition to the surrounding pixel change amount $B_{hor}$ calculated by equation (5) in the horizontal direction and the surrounding pixel change amount $B_{ver}$ calculated by equation (6) in the vertical direction, a surrounding pixel change amount $B_{sla}$ in the diagonally-right-up direction and a surrounding pixel change amount $B_{bac}$ in the diagonally-right-down direction are calculated respectively by the following equations (7) and (8).

$$B_{sla} = \left\{ 1 - \left| \frac{IA_{sla} - IB_{sla}}{IMG\_MAX} \right| \right\}^2 \quad (7)$$

$$B_{bac} = \left\{ 1 - \left| \frac{IA_{bac} - IB_{bac}}{IMG\_MAX} \right| \right\}^2 \quad (8)$$

The surrounding pixel change amount $B_{dir}$ calculated in this manner is defined to be one when the surrounding pixels $IA_{dir}$ and $IB_{dir}$ opposite each other across the pixel of interest as a center have the same pixel value and to be zero when one of the mutually-opposite surrounding pixels $IA_{dir}$ and $IB_{dir}$ is zero and the other one is IMG_MAX. In other words, while the surrounding pixel change amount $B_{dir}$ calculated by equations (5) to (8) becomes one when the balance degree of the mutually-opposite surrounding pixels $IA_{dir}$ and $IB_{dir}$ is maximum, the surrounding pixel change amount $B_{dir}$ becomes zero when the balance degree of the mutually-opposite surrounding pixels $IA_{dir}$ and $IB_{dir}$ is minimum, so that the balance degree is indicated by a range expressed by zero to one.

In addition, in the case where the pixel of interest IP is located at a margin of the image and any of the surrounding pixels gets out of the range of the image, a surrounding pixel is set through the folding at the margin of the image and the surrounding pixel change amount is calculated similarly to the manner explained in the calculation of the pixel value change amount with the surrounding pixels.

Next to step S103 explained above, the weighted change amount calculator 104a calculates a weighted pixel value change amount based on the pixel value change amount calculated by the change amount calculator 102 with the surrounding pixels and the surrounding pixel change amount calculated by the inter-surrounding-pixel change amount calculator 103 (step S104). First, in the case of calculating the pixel value change amount and the surrounding pixel change amount in each of the two directions, i.e., the horizontal and the vertical directions (see FIG. 4), the weighted pixel value change amount is also calculated in each of the horizontal and the vertical directions. In this case, when the weighted pixel value change amount in the horizontal direction is set to be $V'_{hor}$ and the weighted pixel value change amount in the vertical direction is set to be $V'_{ver}$, the weighted pixel value change amounts $V'_{hor}$ and $V'_{ver}$ are calculated respectively by the following equations (9) and (10).

$$V'_{hor} = B_{hor} \times V_{hor} \quad (9)$$

$$V'_{ver} = B_{ver} \times V_{ver} \quad (10)$$

In contrast, in the case of calculating the pixel value change amount with the surrounding pixels and the surrounding pixel change amount in each of the four directions, i.e., the horizontal direction, the vertical direction, the diagonally-right-up direction, and the diagonally-right-down direction (see FIG. 5), the weighted pixel value change amount is also calculated in each of the horizontal direction, the vertical direction, the diagonally-right-up direction, and the diagonally-right-down direction. In this case, in addition to the weighted pixel value change amount $V'_{hor}$ calculated by equation (9) in the horizontal direction and the weighted pixel value change amount $V'_{ver}$ calculated by equation (10) in the vertical direction, a weighted pixel value change amount $V'_{sla}$ in the diagonally-right-up direction and a weighted pixel value change amount $V'_{bac}$ in the diagonally-right-down direction are calculated respectively by the following equations (11) and (12).

$$V'_{sla} = B_{sla} \times V_{sla} \quad (11)$$

$$V'_{bac} = B_{bac} \times V_{bac} \quad (12)$$

Figure 8A:
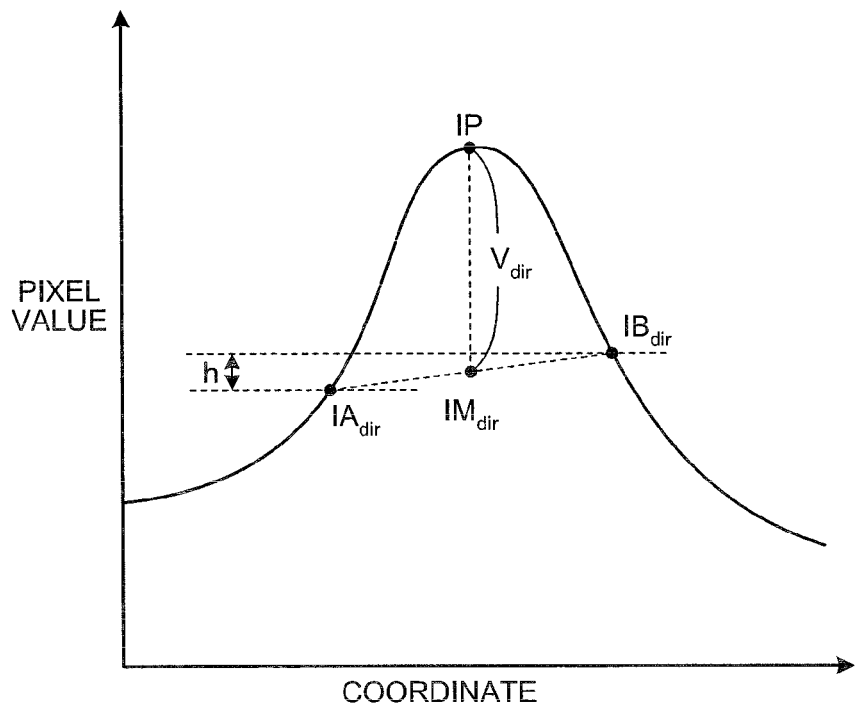
FIG. 8A shows an example (first example) of weighting a change amount of surrounding pixels.
Figure 8B:
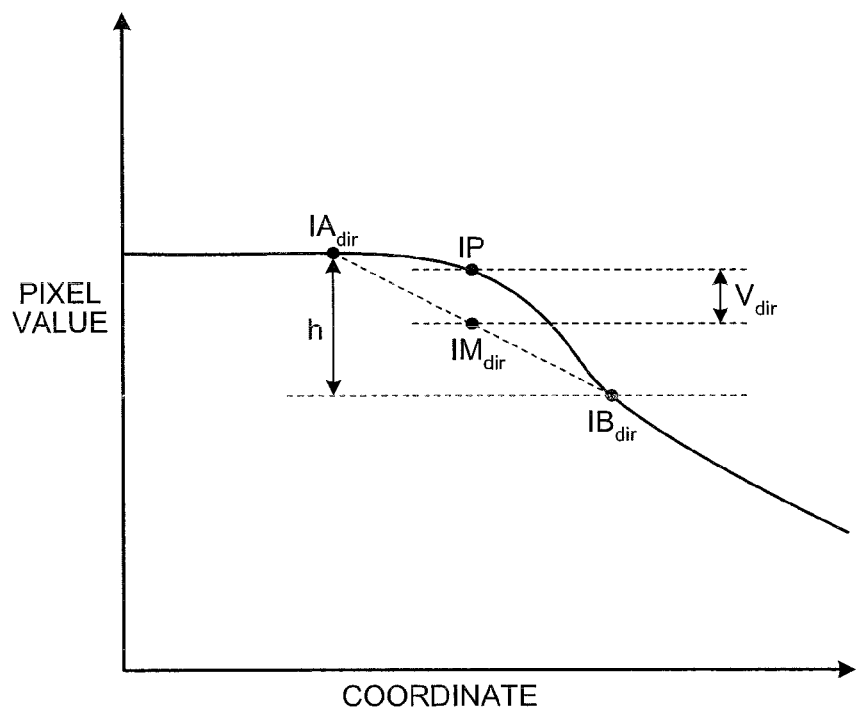
FIG. 8B shows an example (second example) of weighting a change amount of surrounding pixels.

FIGS. 8A and 8B show examples of weighting the surrounding pixel change amount. FIG. 8A shows a case where the surrounding pixels $IA_{dir}$ and $IB_{dir}$ opposite to each other are almost balanced and the pixel of interest IP presents a change towards the same direction as the surrounding pixels $IA_{dir}$ and $IB_{dir}$, the change being a convex. In the case shown in FIG. 8A, since a change amount h ($=|IA_{dir}-IB_{dir}|$) between the surrounding pixels $IA_{dir}$ and $IB_{dir}$ is small with respect to the pixel value change amount $V_{dir}$ of the pixel of interest IP with the surrounding pixels, the surrounding pixel change amount $B_{dir}$ is a value close to one (see equations (5) to (8)). Thus, the weighted pixel value change amount $V'_{dir}$ ($=B_{dir} \times V_{dir}$) is also set as a value close to the pixel value change amount $V_{dir}$ with the surrounding pixels (see equations (9) to (12)).

On the other hand, FIG. 8B shows a case where the surrounding pixels $IA_{dir}$ and $IB_{dir}$ opposite to each other are unbalanced. In the case shown in FIG. 8B, since the change amount h ($=|IA_{dir}-IB_{dir}|$) between the surrounding pixels $IA_{dir}$ and $IB_{dir}$ is large with respect to the pixel value change amount $V_{dir}$ of the pixel of interest IP with the surrounding pixels, the surrounding pixel change amount $B_{dir}$ is a value close to zero (see equations (5) to (8)). Thus, the weighted pixel value change amount $V'_{dir}$ ($=B_{dir} \times V_{dir}$) is set as a small value with respect to the pixel value change amount $V_{dir}$ with the surrounding pixels (see equations (9) to (12)).

Subsequently, the change pixel extracting unit 104b determines whether or not the weighted pixel value change amount $V'_{dir}$ calculated by the weighted change amount calculator 104a is within a predetermined range to extract a pixel of interest which shows a change corresponding to the range as a pixel value change pixel (step S105). Specifically, when values of all directions are larger than a predetermined convex threshold value (ConvexityTh) with respect to the weighted pixel value change amount $V'_{dir}$ calculated for each direction, the pixel of interest IP is determined to be a convex with respect to the surroundings. Besides, when values of all directions are smaller than a predetermined concave threshold value (ConcaveTh), the pixel of interest IP is determined to be a concave with respect to the surroundings. To sum up this as (1-1) the case of two directions and (1-2) the case of four directions, the following are true.

(1-1) In the Case of Two Directions

If $V'_{hor}>$ConvexityTh and $V'_{ver}>$ConvexityTh, then the pixel of interest IP shows a convex with respect to the surroundings.

If $V'_{hor}<$ConcaveTh and $V'_{ver}<$ConcaveTh, then the pixel of interest IP shows a concave with respect to the surroundings.

(1-2) In the Case of Four Directions

If $V'_{hor}>$ConvexityTh, $V'_{ver}>$ConvexityTh, $V'_{sla}>$ConvexityTh, and $V'_{bac}>$ConvexityTh, then the pixel of interest IP shows a convex with respect to the surroundings.

If $V'_{hor}<$ConcaveTh, $V'_{ver}<$ConcaveTh, $V'_{sla}<$ConcaveTh, and $V'_{bac}<$ConcaveTh, then the pixel of interest IP shows a concave with respect to the surroundings.

Then, a convex binary image and a concave binary image are created, the convex binary image being recorded as a binary image in which a pixel showing a convex with respect to the surroundings is set to one and a pixel not showing a convex with respect to the surrounding is set to zero, and the concave binary image being recorded as a binary image in which a pixel showing a concave with respect to the surroundings is set to one and a pixel not showing a concave with respect to the surrounding is set to zero.

By performing step S105 explained above, it is possible to determine whether or not the pixel of interest IP has a significant value as a candidate lesion.

Next, the pixel-value-change recording amount calculator 104c calculates a pixel-value-change recording amount $V_r$ to be recorded, as the pixel value change amount of the pixel value change pixel, i.e., the pixel of interest determined at step S105 to be a convex or a concave with respect to the surroundings, to the storage unit 11 (step S106). In the case of calculating the pixel-value-change recording amount $V_r$ in the two directions, i.e., the horizontal and the vertical directions, when the pixel of interest is determined to be a convex or a concave with respect to the surroundings, the pixel-value-change recording amount $V_r$ is calculated by the following equation (13).

$$V_r = \frac{V'_{hor} + V'_{ver}}{2} \qquad (13)$$

Besides, in the case of calculating the pixel-value-change recording amount $V_r$ in the four directions, i.e., the horizontal direction, the vertical direction, the diagonally-right-up direction, and the diagonally-right-down direction, the pixel-value-change recording amount $V_r$ is calculated by the following equation (14).

$$V_r = \frac{V'_{hor} + V'_{ver} + V'_{sla} + V'_{bac}}{2} \qquad (14)$$

It should be noted that the pixel-value-change recording amount $V_r$ of the pixel of interest IP which is determined to have neither a convex nor a concave with respect to the surroundings is stored as zero in the storage unit 11.

The calculation of the pixel-value-change recording amount $V_r$ at step S106 explained here is not limited to the method described above, and a maximum value or a minimum value among the weighted pixel value change amounts $V'_{dir}$ of all directions may be adopted.

The processing at steps S102 to S106 described above (the processing included in a broken line area SP in FIG. 3) is performed with respect to all pixels of interest IP. Specifically, it is only necessary that the processing at steps S102 to S106 is performed in sequence by treating all pixels included in the image obtained at step S101, for example, as a pixel of interest IP.

Figures 9, 10:
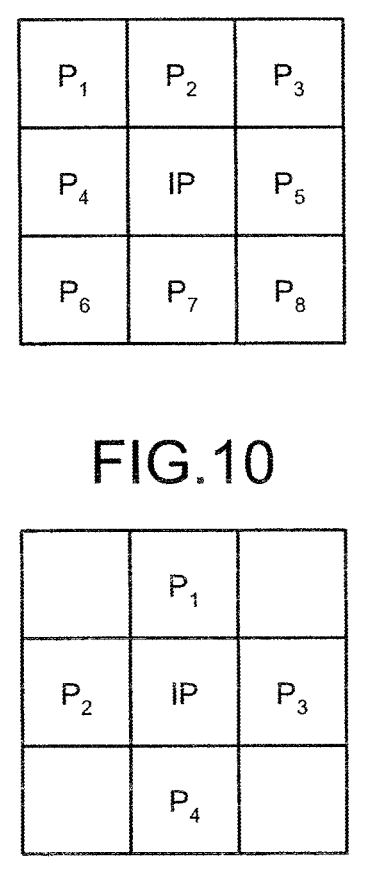

Subsequently, the candidate lesion region detector 104 performs a region division with respect to each of the pixel having a convex and the pixel having a concave to extract a candidate lesion region (step S107). Specifically, the region division is performed by using the convex binary image and the concave binary image created by the change pixel extracting unit 104b so that, in eight neighborhoods $P_1$ to $P_8$ with respect to the pixel of interest IP as shown in FIG. 9, a pixel to which one is recorded among the eight neighborhoods $P_1$ to $P_8$ constitutes the same region as the pixel of interest IP when the pixel of interest IP is one. Here, an image obtained by dividing a convex region from the convex binary image and labeling each divided region is treated as a convex region image, an image obtained by dividing a concave region from the concave binary image and labeling each divided region is treated as a concave region image, and the extracted convex region and the concave region are treated as a candidate lesion region together.

Thereafter, the feature extracting unit 105 calculates a feature amount of each candidate lesion region obtained at step S107 (step S108). As the feature amount to be calculated here, a within-region pixel value average ($R_{abs\_m}$, $G_{abs\_m}$, $B_{abs\_m}$), a within-region pixel value change amount average ($R_{var\_m}$, $G_{var\_m}$, $B_{var\_m}$), a region area $S_{\_m}$, a region boundary length $L_{\_m}$, a region long side length $L_{l\_m}$, a region short side length $L_{s\_m}$, a region's long-side-to-short-side ratio $L_{r\_m}$, a region's contour part edge intensity $E_{\_m}$, and a region circularity $C_{\_m}$ can be listed. It should be noted that a suffix "m" represents a region number. Each feature amount will be explained below.

The within-region pixel value average ($R_{abs\_m}$, $G_{abs\_m}$, $B_{abs\_m}$) is calculated by obtaining a summation of pixels belonging to the same region in each of the channels R, G, and B and dividing the summation by a region area.

In the case of calculating the within-region pixel value average (Rvar$_{\_m}$, Gvar$_{\_m}$, Bvar$_{\_m}$), since the pixel-value-change recording amount $V_r$ for the G channel is already obtained at step S106, after the pixel-value-change recording amount $V_r$ for each of the remaining R and B channels is calculated here similarly to the G channel, the within-region pixel value change amount average ($R_{var\_m}$, $G_{var\_m}$, $B_{var\_m}$) is calculated by obtaining a summation of the pixel-value-change recording amounts $V_r$ of pixels belonging to the same region for each of the R, G, and B channels and then dividing the summation by the region area. Here, on the occasion of calculating the pixel-value-change recording amount in the R and B channels, not all the pixels are targeted and only a pixel extracted as having a convex or a concave in the G channel (a pixel to which one is set in the convex binary value image and the concave binary value image) is targeted to realize a high-speed processing.

The region area $S_{\_m}$ is calculated by counting the number of pixels belonging to the same region.

The region boundary length $L_{\_m}$ is obtained by treating, as a pixel at a region contour part, a pixel which verges on a background pixel or a pixel to which a different label number is assigned in the four neighborhood pixels $P_1$ to $P_4$ with respect to the pixel of interest IP as shown in FIG. 10 and by counting the number of the pixels at the region contour part.

The long side length $L_{l\_m}$ and the short side length $L_{s\_m}$ of each region are calculated by capturing the region through an approximation by a rectangle based on the region boundary length $L_{\_m}$ and the region area $S_{\_m}$ as shown in equations (15) and (16) below.

$$L_{l\_m} = \frac{L_{\_m} + \sqrt{L_{\_m}^2 - 16 S_{\_m}}}{4} \qquad (15)$$

$$L_{s\_m} = \frac{S_{\_m}}{L_{l\_m}} \qquad (16)$$

The region's long-side-to-short-side ratio $L_{r\_m}$ is calculated as shown in equation (17).

$$L_{r\_m} = \frac{L_{l\_m}}{L_{s\_m}} \quad (17)$$

In a calculation of the region's contour part edge intensity $E_{\_m}$, a background pixel or a pixel which verges on another region is first extracted as a pixel at a region contour part pixel with respect to each candidate lesion region. The edge intensity of each pixel is calculated by applying an edge detection filter as shown in FIGS. 11A and 11B to a gray scale image which takes one of the R, G, and B channels or an average of the R, G, and B channels of the body cavity image.

Figure 11A:
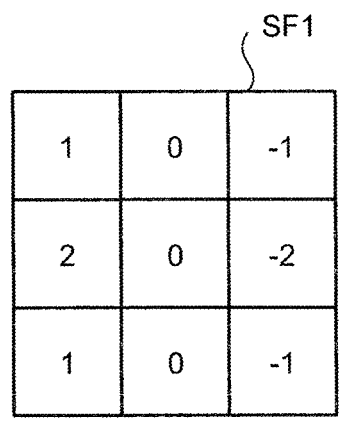
FIG. 11A shows a Sobel filter in a horizontal direction.
Figure 11B:
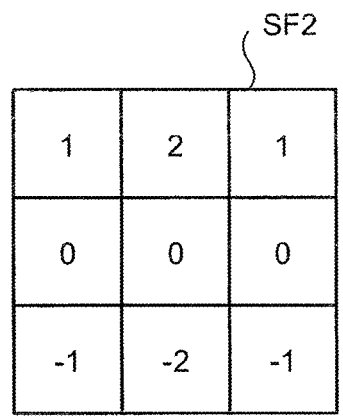
FIG. 11B shows a Sobel filter in a vertical direction.

An edge intensity image $E_I(i)$ via the Sobel filter as a linear differentiation is, by using a convolution output $S1(i)$ of a Sobel filter SF1 in the horizontal direction (x-direction) shown in FIG. 11A and a convolution output $S2(i)$ of a Sobel filter SF2 in the vertical direction (y-direction) shown in FIG. 11B, expressed as shown by the following equation (18) (in which "i" represents a pixel position in the image).

$$E_I(i) = \sqrt{S1(i)^2 + S2(i)^2} \quad (18)$$

Thereafter, a value of an edge intensity image at a pixel position of a region contour part of each candidate lesion region is read out, a summation of the edge intensity values is calculated for each candidate lesion region, and the summation is divided by the boundary length $L_{\_m}$ of each candidate lesion region, so that the following equation (19) is calculated as an edge intensity $E_{\_m}$ of the region contour part.

$$E_{\_m} = \frac{\sum_i E_1(i)}{L_{\_m}} \quad (19)$$

A calculation of the region circularity $C_{\_m}$ is expressed by the following equation (20).

$$C_{\_m} = \frac{4\pi S_{\_m}}{L_{\_m}^2} \quad (20)$$

After step S108 explained above, the lesion detector 106 eliminates a region which is generated by a non-lesion factor in a convex region and a concave region each as a candidate lesion region (steps S109 and S110).

Of the two steps, in performing the elimination (step S109) of the concave region generated by a non-lesion, a feature amount of each concave region is compared with a distribution of a master data feature amount to determine whether the region is a lesion or a non-lesion. For example, in the case of determining whether a targeted candidate lesion region is a lesion or a non-lesion by using the within-region pixel value average $x=(R_{abs\_m}, G_{abs\_m}, B_{abs\_m})$, a sample region for each of lesion types including a bleeding is collected and a pixel value average $\mu_k$ and a pixel value covariance $\Sigma_k$ are calculated as master data (here, "k" represents a group number of master data). It should be noted that samples of the same lesion type or samples whose pixel value averages are close to each other in the same lesion type are treated as one group and each group is assigned with a group number "k" in the first embodiment. Besides, a sample of a concave region which is not a candidate lesion region is also collected, samples are grouped for each factor extracted as a concave region or samples whose pixel value averages are close to each other are grouped as the same group, and a pixel value average $\mu_i$ and a pixel value covariance $\Sigma_i$ are calculated (here, "i" represents a number of a group which is generated by grouping samples in a concave region of a non-candidate lesion region).

By treating the master data distribution as a standard, a probability that a concave region as a candidate lesion region arises from the distribution of each master data group is calculated by the following equations (21) and (22).

$$p(k \mid x) = \frac{1}{(2\pi)^{n/2} |\sum_k|^{1/2}} \exp\left\{-\frac{1}{2}(x-\mu_k)^t \left(\sum_k\right)^{-1}(x-\mu_k)\right\} \quad (21)$$

$$p(i \mid x) = \frac{1}{(2\pi)^{n/2} |\sum_i|^{1/2}} \exp\left\{-\frac{1}{2}(x-\mu_i)^t \left(\sum_i\right)^{-1}(x-\mu_i)\right\} \quad (22)$$

Here, "n" represents a dimension number of the feature amount and the "n" is three in the case of the within-region pixel value average x. Based on the probability $p(k|x)$, calculated by equation (21), of arising from a lesion group and the probability $p(i|x)$, calculated by equation (22), of arising from a non-lesion group, a probability $P_{k=a}$ of being ascribed to a given pathological condition "a" is calculated by the following equation (23).

$$P_{k=a} = \frac{p(k=a \mid x)}{\sum p(i \mid x) + \sum p(k \mid x)} \quad (23)$$

Above equation (23) indicates the following. A probability that a candidate lesion region having a feature amount variable x arises from a distribution of a group of the pathological condition "a" among lesion groups is expressed by $p(k=a|x)$. A whole sum of probabilities of arising from a distribution of non-lesion groups is expressed by $\Sigma p(i|x)$ and a whole sum of probabilities of arising from a distribution of lesion groups is expressed by $\Sigma p(k|x)$. Thus, the probability $P_{k=a}$ of being ascribed to the given pathological condition "a" is calculated by regularizing, with respect to the candidate lesion region having the feature amount variable x, the probability of arising from the group of the pathological condition "a" by the whole sum of the probabilities of arising from the entire groups.

In accordance with the details described above, a probability of being ascribed to each pathological condition for each candidate lesion region is calculated, and when a probability with a certain pathological condition which shows a maximum value is set as $p(k=a_{max}|x)$ and the value is equal to or less than a predetermined threshold value LesionProbTh, i.e., $p(k=a_{max}|x) \leq$ LesionProbTh is true, the corresponding concave region is eliminated from the candidate lesion region.

Subsequently, with respect to the convex regions remaining as a candidate lesion region, an elimination of a convex region generated by a non-lesion is performed (step S110). Similarly to the above-described non-lesion region determination with respect to the concave region, a probability of arising from each group in a prepared distribution of master data is calculated with respect to convex regions remaining as a candidate lesion region to determine whether the region is a lesion or a non-lesion.

As the feature amount to be used for the lesion/non-lesion determination of the candidate lesion region, not only the within-region pixel value average $(R_{abs\_m}, G_{abs\_m}, B_{abs\_m})$ of a target region but also any one of the within-region pixel value change amount average $(R_{var\_m}, G_{var\_m}, B_{var\_m})$, the region area $S_{\_m}$, the region boundary length $L_{\_m}$, the region long side length $L_{l\_m}$, the region short side length $L_{s\_m}$, the region's long-side-to-short-side ratio $L_{r\_m}$, the region's contour part edge intensity $E_{\_m}$, and the region circularity $C_{\_m}$ may be used, or an arbitrary combination of them may be used.

It should be noted that the processing at step S109 with respect to a concave region and the processing at step S110 with respect to a convex region may be performed in a reverse order or in parallel.

Lastly, the concave region and the convex region remaining as a lesion region are displayed on the display unit 107 as a result of the lesion detection (step S111). In this display, a predetermined pixel value is allotted to a pixel belonging to the concave region, another predetermined pixel value different from the pixel value allotted to the concave region is allotted to a pixel belonging to the convex region, and a background color is provided to other pixels, to be displayed.

Incidentally, the display method in the display unit 107 is not limited to the method described above. For example, though groups to which the concave region and the convex region belong respectively are determined in the lesion/non-lesion determination based on the master data at steps S109 and S110 described above, a pixel value corresponding to each group (corresponding to a lesion kind) may be allotted and displayed. Moreover, with respect to the body cavity image, a pixel value corresponding to each group to which each region belongs may be superimposed on a pixel position at a contour part of the concave region and the convex region remaining as the lesion region and may be displayed.

According to the first embodiment of the present invention described above, it becomes possible to extract a region which presents a change in a pixel value with its periphery in an image in a short processing time period, and thereby to detect a candidate lesion region with a robustness against environmental differences in obtaining images.

Besides, it is possible according to the first embodiment to realize an image processing apparatus which performs a lesion detection at high speed and with high detection performance by using a region feature amount and eliminating a region which is extracted as a candidate lesion region in spite of essentially being a normal part from a candidate lesion region.

An image processing program according to the first embodiment can also be recorded to computer-readable recording media such as a flexible disc, a CD-ROM, a DVD-ROM, a flash memory and distributed widely. In this sense, the image processing apparatus 1 may be provided with a subsidiary storage device which can read out any of the listed various recording media.

Second Embodiment

Figure 12:
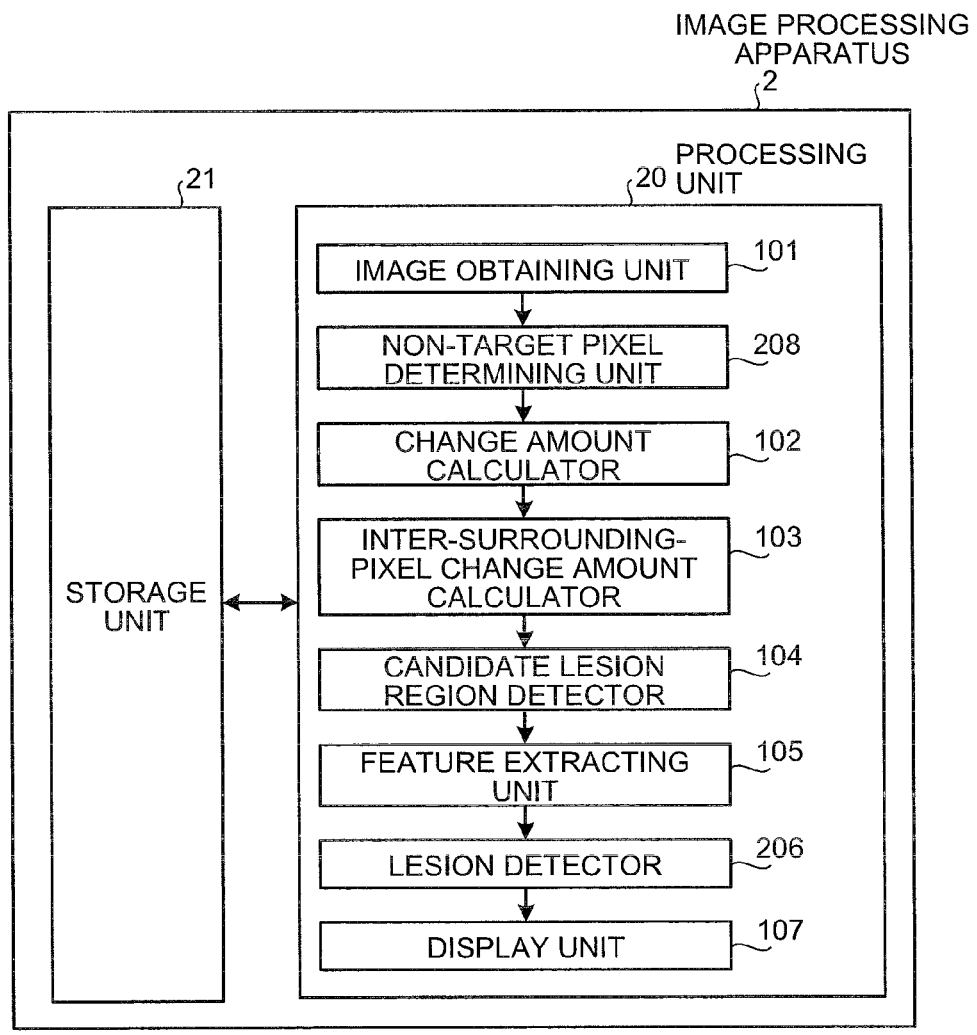
FIG. 12 is a block diagram of a configuration of an image processing apparatus according to a second embodiment of the present invention.

FIG. 12 is a block diagram of a configuration of an image processing apparatus according to a second embodiment of the present invention. An image processing apparatus 2 shown in FIG. 12 includes a processing unit 20 and a storage unit 21 which stores image information of captured body cavity images. The image processing apparatus 2 is constituted by a computer provided with a CPU, ROM, RAM, and the like.

The processing unit 20 includes the image obtaining unit 101, the change amount calculator 102, the inter-surrounding-pixel change amount calculator 103, the candidate lesion region detector 104, the feature extracting unit 105, and the display unit 107, each of which functions similarly to the image processing apparatus 1 according to the first embodiment described above. In addition, the processing unit 20 includes a non-target pixel determining unit 208 which determines a non-target pixel to be excluded as a target which is subjected to the calculation by the change amount calculator 102 and the inter-surrounding-pixel change amount calculator 103, and a lesion detector 206 which detects a lesion region based on the result extracted by the feature extracting unit 105.

Figure 13:
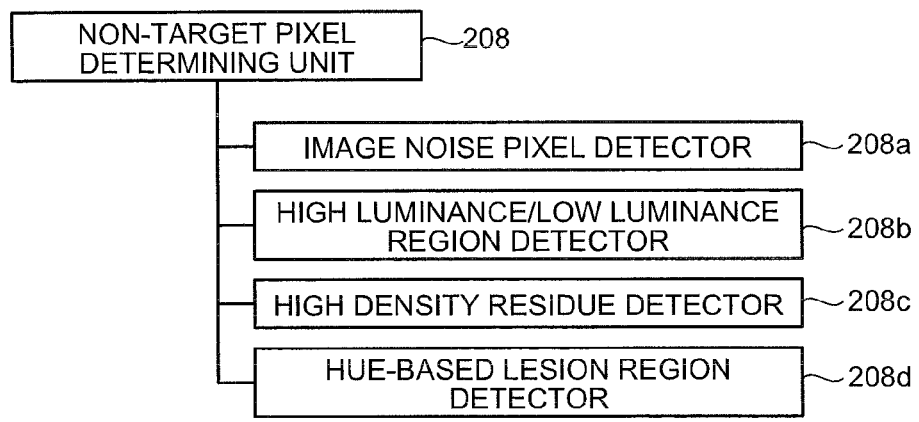
FIG. 13 is a block diagram of a configuration of a non-target pixel determining unit.

As shown in FIG. 13, the non-target pixel determining unit 208 includes an image noise pixel detector 208a, a high luminance/low luminance region detector 208b, a high density residue detector 208c, and a hue-based lesion region detector 208d which detect, as a non-target pixel, an image noise pixel, a high luminance pixel or a low luminance pixel, a pixel constituting a food residue, and a pixel region having a hue of a significant lesion origin, respectively.

Figure 14:
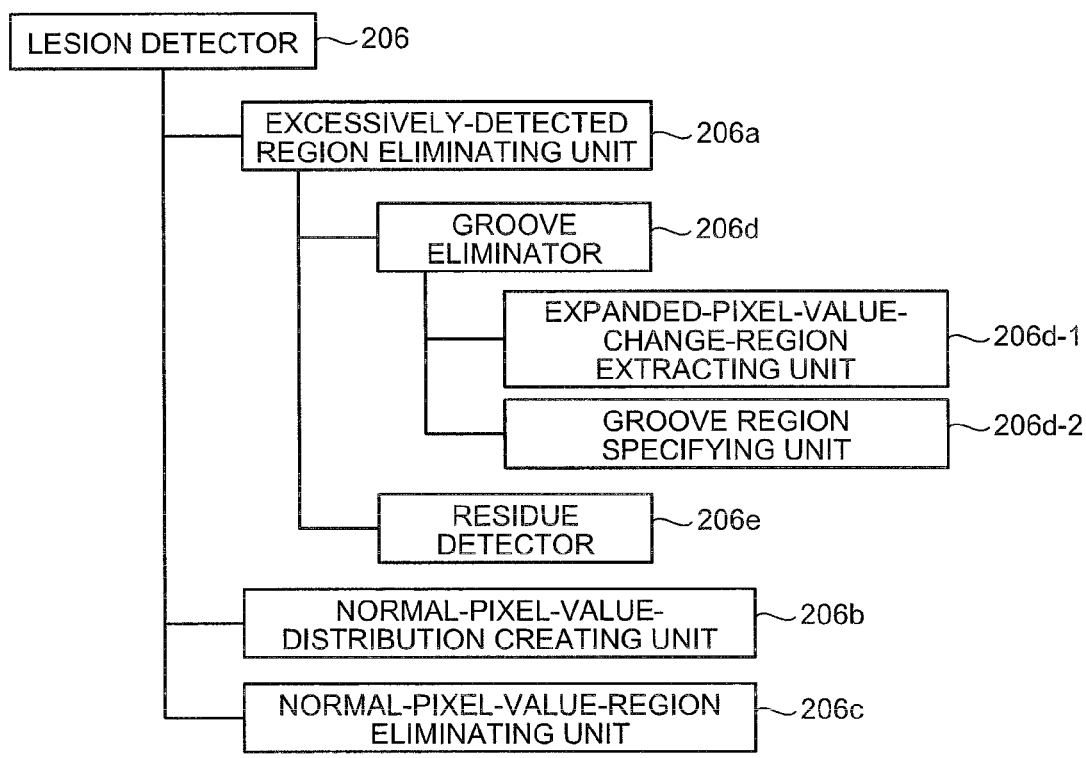
FIG. 14 is a block diagram of a configuration of a lesion detector.

As shown in FIG. 14, the lesion detector 206 includes: an excessively-detected-region eliminating unit 206a which eliminates, in the candidate lesion region, a region which is detected due to a structure within the body cavity or due to a substance that can be contained within the body cavity; a normal-pixel-value-distribution creating unit 206b which treats, among pixels except for non-target pixels, a value of a pixel in a region other than the candidate lesion region and a value of a pixel in a region belonging to a predetermined non-lesion group in the candidate lesion region in the body cavity image as a pixel value of a normal organ tissue in a target image, and creates a normal pixel value distribution based on the pixel value of the normal organ tissue; and a normal-pixel-value-region eliminating unit 206c which calculates a probability that the remaining candidate lesion region belongs to the normal pixel value distribution described above based on the pixel value average of each candidate lesion region, and eliminates the corresponding region from the candidate lesion region when the calculated probability is more than a predetermined threshold value.

The excessively-detected-region eliminating unit 206a includes a groove eliminating unit 206d which eliminates a shadow part due to a groove on an organ wall from a candidate lesion region, and a residue detector 206e which detects a region generated by a food residue staining in an organ inside the body in the candidate lesion region based on the region's contour part edge intensity and eliminates the detected region from the candidate lesion region. Of the two units, the groove eliminating unit 206d includes: an expanded-pixel-value-change-region extracting unit 206d-1 which extracts a pixel of interest as an expanded pixel value change region when the weighted pixel value change amount for each direction calculated by the weighted change amount calculator 104a in the candidate lesion region detector 104 exceeds a predetermined threshold value in any one of directions, extracts the region as an expanded pixel value change region by performing a region division in which adjacent expanded pixel value change pixels are treated as the same region, and calculates a feature amount of the extracted expanded pixel value change region; and a groove region specifying unit 206d-2 which specifies a groove region based on the feature amount of the expanded pixel value change region calculated by the expanded-pixel-value-change-region extracting unit 206d-1.

Figure 15:
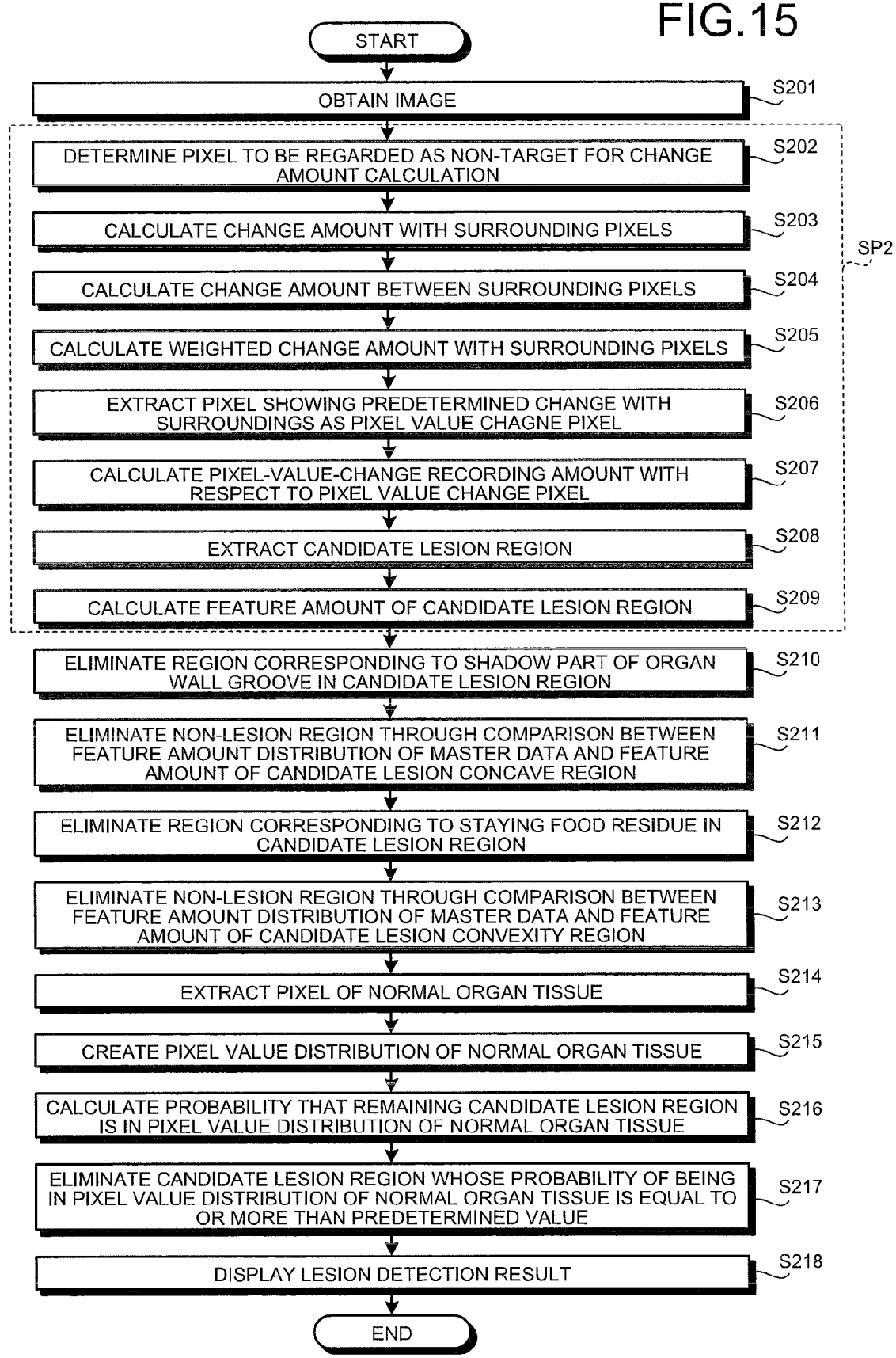
FIG. 15 is a flowchart of a summary of an image processing method according to the second embodiment of the present invention.

FIG. 15 is a flowchart of a summary of a processing in an image processing method performed by the image processing apparatus 2. The summary of the processing in the image processing method according to the second embodiment will be explained below with reference to FIG. 15.

Similarly to the first embodiment, the image obtaining unit 101 obtains an image captured in an inside of a body cavity (a body cavity image) from the storage unit 21 (step S201).

Thereafter, the non-target pixel determining unit 208 detects and determines a pixel to be excluded as a detection target pixel constituting a candidate lesion region in the image (step S202). As a non-target pixel determined at step S202, four kinds of pixels can be listed, i.e., an image noise pixel, a high luminance or low luminance pixel, a pixel constituting a food residue staying inside the organ in high density, and a pixel region having a hue of a significant lesion origin. A summary of a processing of detecting each non-target pixel will be explained below.

Figure 16A:
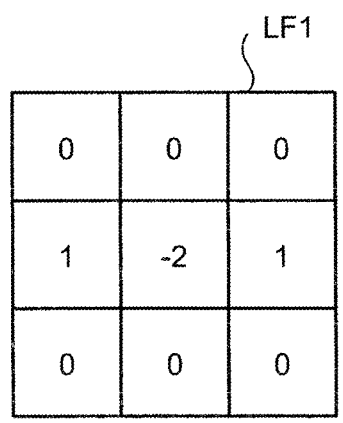
FIG. 16A shows a configuration of a Laplacian filter in the horizontal direction.
Figure 16B:
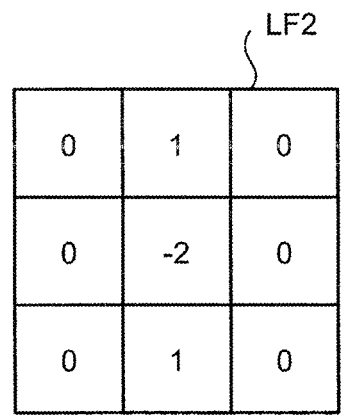
FIG. 16B shows a configuration of a Laplacian filter in the vertical direction.

First, a detection of the image noise pixel will be explained. The image noise pixel indicates a noise which occurs, due to noise-inducing causes such as a physical impact, an electrical factor, and an optical factor, in an image obtained by a device that captures images of organs inside the living body. Since the image noise pixel has a pixel value unrelated to a pixel constituting the organ captured inside the body, a steep change in a pixel value is seen among pixels adjacent to the image noise. Therefore, the image noise pixel detector 208a applies a Laplacian filter LF1 in the horizontal direction shown in FIG. 16A and a Laplacian filter LF2 in the vertical direction shown in FIG. 16B to a gray scale image which is obtained based on any one of the R, G, and B channels or an average of the R, G, and B channels of the image, and detects a pixel whose maximum output value in the horizontal or vertical direction exceeds a predetermined threshold value as a pixel having an occurrence of an image noise.

Secondly, a detection of the high luminance or low luminance pixel will be explained. The high luminance/low luminance region detector 208b scans each pixel to obtain a pixel value and detects a pixel whose value exceeds a predetermined high luminance threshold value. The detected high luminance pixel, since having a possibility of developing luminance saturation, is eliminated from a subsequent processing. Similarly, a pixel whose value falls below a predetermined low luminance threshold value is also detected. The detected low luminance pixel, since being determined that a lesion part and the like are not caught in a recognizable luminance, is eliminated from the subsequent processing.

Thirdly, a detection of the pixel constituting a food residue staying in an organ in high density will be explained. A part where the food residue is present in high concentration in the image shows a unique color different from the color of the body organ tissue. So, the high density residue detector 208c divides the image into small blocks each of which is formed by a predetermined number of pixels, calculates an average of values of pixels in each small block, detects a small block whose calculated value falls within a pixel value range which is specified in advance as a pixel value peculiar to a food residue, treats the small block as a region where the food residue is present, and eliminates the small block from the subsequent processing.

Lastly, a detection of the pixel having a hue of a significant lesion origin will be explained. The hue-based lesion region detector 208d detects a region having a hue of a significant lesion origin, like a case where blood due to a bleeding in the organ spreads over a wide range on the image. When a large amount of bleeding is recognized in the image, the part shows a specific color different from the color of the body organ tissue because of the blood. Therefore, for the detection of a region having the large amount of bleeding, the image is divided into small blocks each of which is formed by a predetermined number of pixels, an average of values of pixels in each small block is calculated, a small block whose calculated value falls within a pixel value range which is specified in advance as a pixel value peculiar to blood is detected, treats the small block as a region where the large amount of bleeding is present, and eliminates the small block from the subsequent processing. It should be noted that the "region having a hue of a significant lesion origin" is not limited to the case of the bleeding, and may include a case where a body organ is significantly discolored and the like.

Next to step S202 described above, the change amount calculator 102 calculates a pixel value change amount with surrounding pixels (step S203) and the inter-surrounding-pixel change amount calculator 103 calculates a pixel value change amount between the surrounding pixels.

Thereafter, by using the pixel value change amount calculated at step S203 with the surrounding pixels and the surrounding pixel change amount calculated at step S204, the candidate lesion region detector 104 calculates a weighted change amount with the surrounding pixels (step S205), extracts a pixel of interest which shows a predetermined change from the surroundings as a pixel value change pixel (step S206), and calculates a pixel-value-change recording amount with respect to the extracted pixel value change pixel (step S207).

Then, with respect to the pixel of interest which shows the predetermined change with the surroundings, a candidate lesion region is extracted through a region division by integrating adjacent pixels as one region and labeling each region (step S208), and the feature extracting unit 105 calculates a feature amount of each extracted region (step S209).

It should be noted that the processing at steps S203 to S209 explained above (the processing included in broken line area SP2 in FIG. 15) is performed with respect to all pixels of interest IP, similarly to the processing at steps S102 to S108 in the first embodiment described above.

In the first embodiment described above, a feature amount extracted for each candidate lesion region is compared with a distribution of a master data feature amount to perform the lesion/non-lesion determination. On this occasion, an overlap is present in a distribution of a lesion group and a non-lesion group in the distribution of the master data feature amount. Such an overlap occurs even in a region belonging to the same lesion or to a non-lesion group because there is a variation in environment where each image is obtained when the master data is obtained from various sample images and a feature amount of the overlap tends to be distributed in a relatively wide range. Therefore, to avoid failing to detect and overlooking a region of a lesion origin, i.e., to avoid a degradation of a true positive (TP) in the lesion detection, the lesion region detection is performed to some extent in the first embodiment in such a way that a region of not being lesion origin is detected as a lesion, i.e., a false positive (FP) is generated. In contrast, the second embodiment is provided with a function of reducing the false positive. As a processing to be performed after step S209, a specific processing for reducing the false positive will be explained below.

At step S210, the groove eliminating unit 206d eliminates a concave region generated at a shadow part of a groove on the organ wall from a candidate lesion region (step S210). By taking it into a consideration that a groove generally appears on an image in a way along the organ wall, the expanded-pixel-value-change-region extracting unit 206d-1, if there is a pixel whose pixel value change amount is smaller than a predetermined concave threshold value ConcaveTh in any one direction with respect to the weighted pixel value change amount $V'_{dir}$ calculated in each direction, extracts the pixel, performs a region division in which adjacent pixels among extracted pixels are treated as one region, and thereby extracts an expanded concave region (expanded pixel value change region) in which extracted pixels are coupled as one region at a part of the groove. An image to which the expanded concave region is recorded is treated as an expanded concave region extraction image. A determination of a pixel to be extracted as a pixel constituting the expanded concave region is performed in each of the case of (2-1) two directions and the case of (2-2) four directions in a way below.

(2-1) In the Case of Two Directions

If $V'_{hor}$<ConcaveTh or $V'_{ver}$<ConcaveTh, then the pixel of interest IP shows a concave with respect to the surroundings.

(2-2) In the Case of Four Directions

If $V'_{hor}$<ConcaveTh, $V'_{ver}$<ConcaveTh, $V'_{sla}$<ConcaveTh, or $V'_{bac}$<ConcaveTh, then the pixel of interest IP shows a concave with respect to the surroundings.

The expanded-pixel-value-change-region extracting unit 206d-1 calculates a region area $S_{\_n}$, region boundary length $L_{\_n}$, a region long side length $L_{l\_n}$, a region short side length $L_{s\_n}$, and a region's long-side-to-short-side ratio $L_{r\_n}$ with respect to the expanded concave region. Here, a suffix "n" represents a region number of the expanded concave region. In extracting the expanded concave region, an overlapping area of each concave region extracted as a candidate lesion region with the expanded concave region is calculated and an expanded concave region having the maximum overlapping area is treated as a corresponding expanded concave region which corresponds to a concave region as a calculation target.

Figure 17:
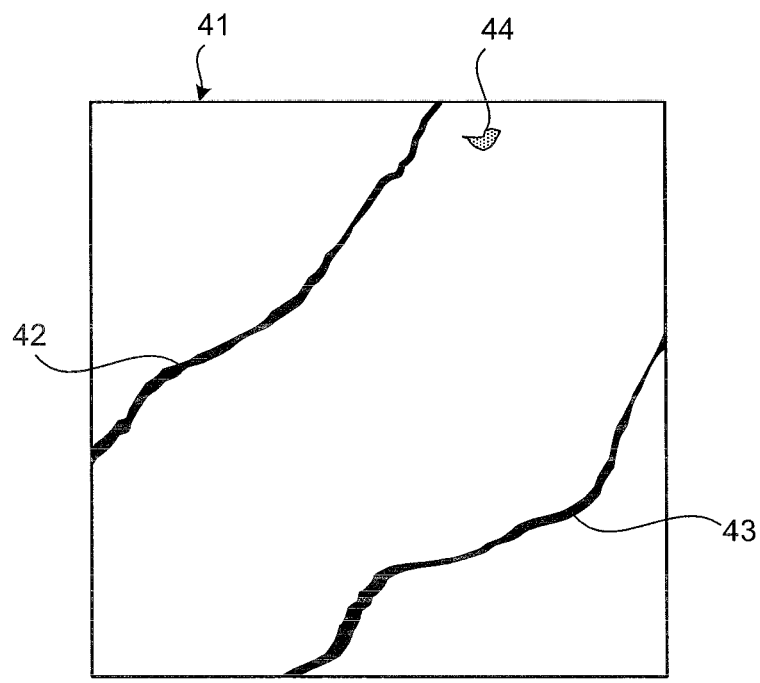
FIG. 17 shows an example of displaying a body cavity image.
Figure 18:
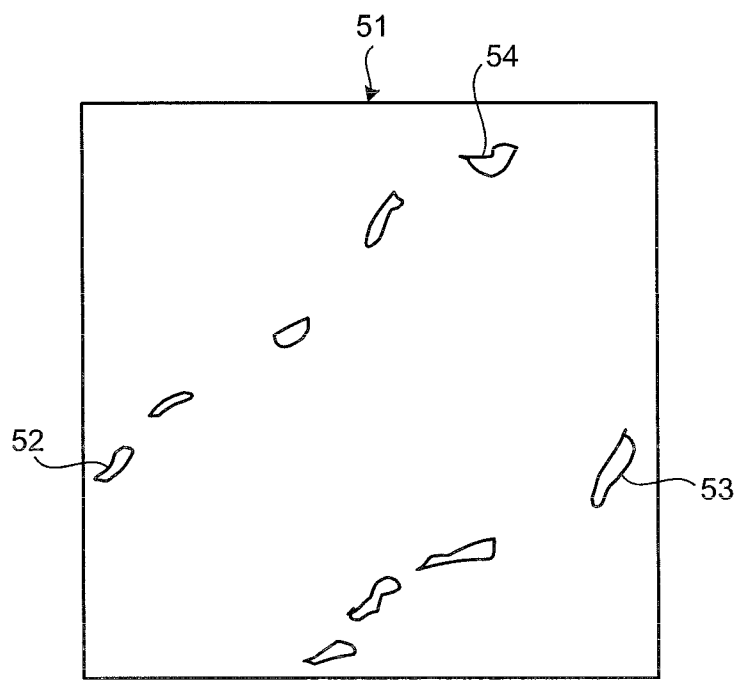
FIG. 18 shows an example of displaying a concave region extraction image.
Figure 19:
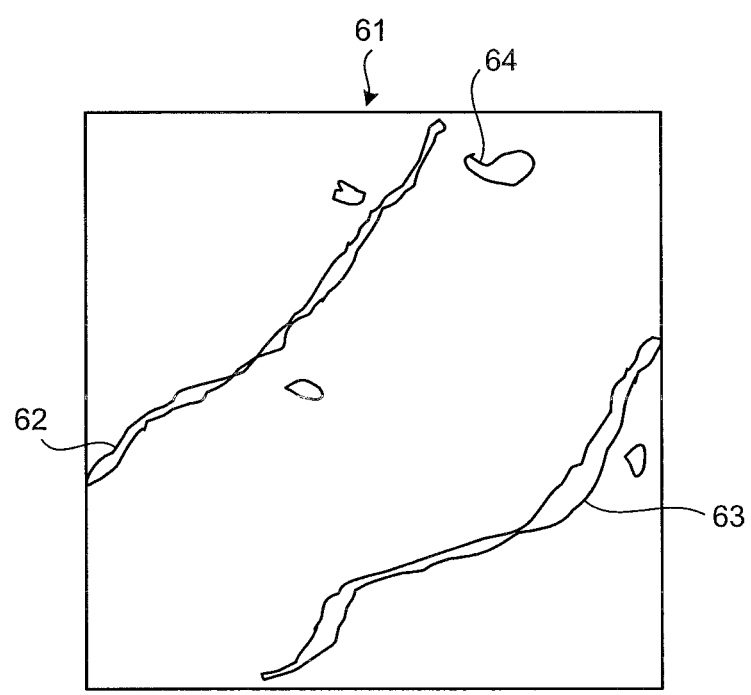
FIG. 19 shows an example of displaying an expanded concave region extraction image.

Here, an example of extracting the expanded concave region will be explained. FIG. 17 shows an example of displaying a body cavity image as an original image. In a body cavity image 41 shown in FIG. 17, a bleeding site is included as well as two organ wall grooves 42 and 43. FIG. 18 shows an example of displaying a concave region extraction image obtained by extracting a concave region from the body cavity image 41 in FIG. 17. In a concave region extraction image 51 shown in FIG. 18, a plurality of concave regions 52, 53, 54, . . . , each of which has nearly equal area are extracted. FIG. 19 shows an example of displaying an expanded concave region extraction image obtained by extracting an expanded concave region with respect to the body cavity image 41 in FIG. 17. An expanded concave region extraction image 61 shown in FIG. 19 has at least an expanded concave region 62 in which concave regions including the concave region 52 are coupled, an expanded concave region 63 in which concave regions including the concave region 53 are coupled, and an expanded concave region 64 in which concave regions including the concave region 54 are coupled.

As seen in FIGS. 18 and 19, the expanded concave regions 62 and 63 corresponding respectively to the organ wall grooves 42 and 43 in the body cavity image 41 are present as long areas which are respectively coupled by the concave regions 52 and 53 in the concave region extraction image 51 in the expanded concave region extraction image 61. On the other hand, the expanded concave region 64 corresponding to the bleeding site 44 in the body cavity image 41 shows no big change compared to the concave region 54 in the concave region extraction image 51. By taking this point into consideration, the expanded-pixel-value-change-region extracting unit 206d-1 calculates various feature amounts described above with respect to the expanded concave region.

After this, when the region long side length $L_{l\_n}$ of the expanded concave region is equal to or more than a predetermined threshold value ExLenTh, and the region's long-side-to-short-side ratio $L_{r\_n}$ is equal to or more than a predetermined threshold value ExLenRateTh, i.e., if $L_{l\_n}$≥ExLenTh and $L_{r\_n}$≥ExLenRateTh, then the groove region specifying unit 206d-2 specifies the expanded concave region as a groove region based on the calculation result described above. On this occasion, when the corresponding expanded concave region is a groove region, the concave region corresponding to the corresponding expanded concave region is eliminated from a candidate lesion region.

Next to step S210 explained above, a feature amount of each of the concave regions remaining as a candidate lesion region is compared to the distribution of the master data feature amount similarly to step S109 in the first embodiment, the lesion/non-lesion determination is performed, and a concave region of a non-lesion origin is eliminated (step S211).

Thereafter, the residue detector 206e eliminates a region corresponding to a staying food residue among regions detected as a candidate lesion region (step S212). Since the food residue and the body organ tissue are different substances and have a distance between their places in spatial depth, pixel values at a border of regions show a steep change, compared to a case of the discoloration of a mucous membrane due to a lesion. Therefore, when the region contour part edge intensity $E_{\_m}$, of a convex region detected as a candidate lesion region is equal to or more than a predetermined threshold value ContourEdgeTh, i.e., if $E_{\_m}$≥ContourEdgeTh, then the convex region is regarded as a region generated by the food residue and eliminated from the candidate lesion region.

Subsequently, a feature amount of each of the convex regions remaining as a candidate lesion region is compared to the distribution of the master data feature amount similarly to step S110 in the first embodiment, the lesion/non-lesion determination is performed, and a convex region of a non-lesion origin is eliminated (step S213).

It should be noted that the processing at steps 210 to S211 with respect to a concave region and the processing at steps S212 to S213 with respect to a convex region may be performed in the reverse order or in parallel.

Next, the normal-pixel-value-distribution creating unit 206b extracts pixels constituting a normal organ tissue in each image based on the results of the non-target pixel determining unit 208, the candidate lesion region detector 104, and the excessively-detected-region eliminating unit 206a (step S214). Specifically, a pixel which is determined, by the non-target pixel determining unit 208, not to be a processing target is eliminated from all pixels in the image as a pixel of a normal organ tissue. Then, the pixel value change pixel which is extracted at step S206 is eliminated. In this regard, since the pixel of the region detected at step S210 among pixel value change pixels as a groove region is a pixel which constitutes a normal organ tissue and whose pixel value is changed compared to peripheral pixels constituting a normal organ tissue due to imaging conditions, the pixel is excluded as a target and treated as a pixel of a normal organ tissue. Moreover, a pixel belonging to a non-lesion group may also be treated as a pixel of a normal organ tissue based on a comparison with the distribution of the master data feature amount.

After step S214, the normal-pixel-value-distribution creating unit 206b creates a pixel value histogram of a pixel of a normal organ tissue in a processing target image based on the distribution of pixel values of pixels which are regarded as pixels of a normal organ tissue (step S215).

Subsequently, the normal-pixel-value-region eliminating unit 206c calculates a probability that the region remaining as a candidate lesion region up to this step is in the pixel value distribution of a normal organ tissue (step S216). Specifically, a probability density in the pixel value histogram of a normal tissue pixel calculated at step S215 with respect to an average value of pixel values in a target region is calculated.

Thereafter, when the probability that the average value of pixel values in the target candidate lesion region calculated at step S216 is in the pixel value distribution of a normal organ tissue is equal to or more than a predetermined value, the normal-pixel-value-region eliminating unit 206c assumes that the region is referred to as a normal tissue and eliminates the region from the candidate lesion region (step S217).

Lastly, a concave/convex region remaining as a candidate lesion region is displayed on the display unit 107 as a lesion region (step S218). It is only necessary that this display is performed similarly to the display according to the first embodiment.

According to the second embodiment explained above, in addition to the elimination of a non-lesion region through the lesion/non-lesion determination based on master data from a candidate lesion region obtained based on a region which shows a change in a pixel value with surroundings in an image, the elimination of a region generated by an organ wall groove or a food residue is performed, besides, a pixel value distribution of a non-lesion normal organ tissue in each image is obtained, and a lesion region is narrowed down based on the distribution, so that a lesion detection with high detection precision while reducing a probability of detecting a non-lesion part as a lesion can be realized.

Third Embodiment

Figure 20:
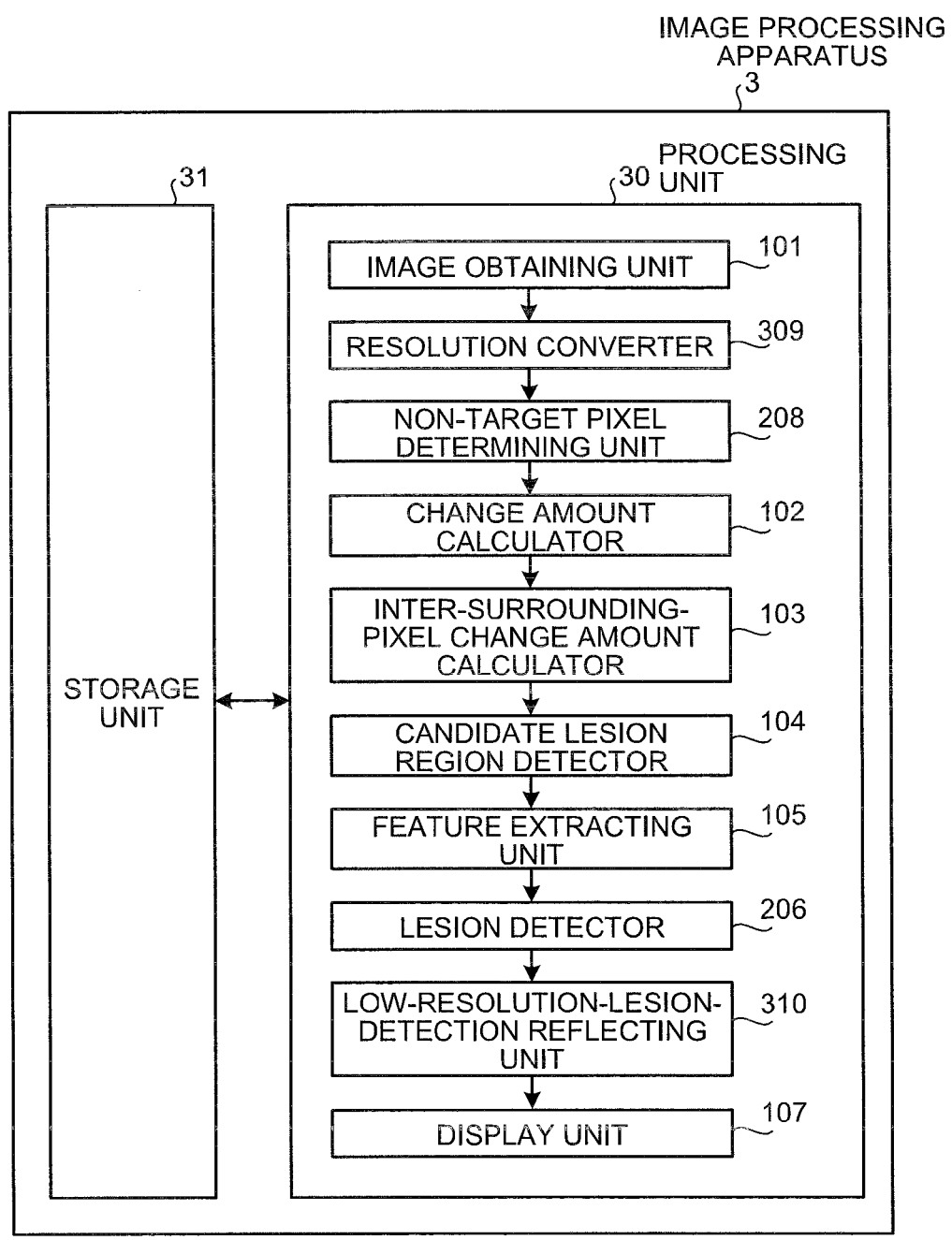
FIG. 20 is a block diagram of a configuration of an image processing apparatus according to a third embodiment of the present invention.

FIG. 20 is a block diagram of a configuration of an image processing apparatus according to a third embodiment of the present invention. An image processing apparatus 3 shown in FIG. 20 includes a processing unit 30 and a storage unit 31 which stores image information of captured body cavity images. The image processing apparatus 3 is constituted by a computer provided with a CPU, ROM, RAM, and the like.

The processing unit 30 includes the image obtaining unit 101, the non-target pixel determining unit 208, the change amount calculator 102, the inter-surrounding-pixel change amount calculator 103, the candidate lesion region detector 104, the feature extracting unit 105, the lesion detector 206, and the display unit 107, each of which functions similarly to the image processing apparatus 2 according to the second embodiment described above. In addition, the processing unit 30 includes a resolution converter 309 which performs a resolution conversion of an image and a low-resolution-lesion-detection reflecting unit 310 which makes a lesion detection result of a low resolution conversion image created by the resolution converter 309 reflected in a lesion detecting processing in an image of one-stage higher resolution.

Figure 21:
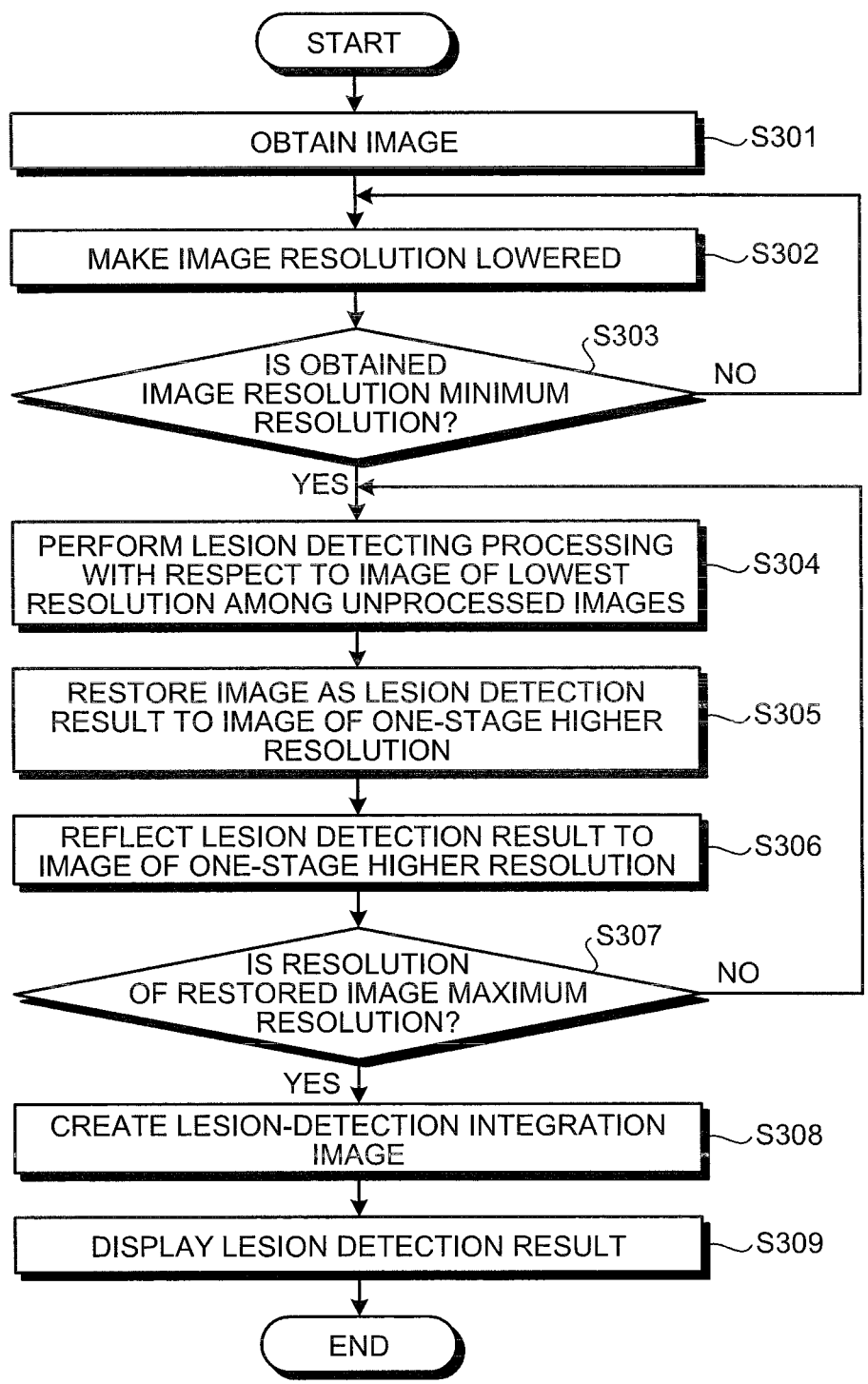
FIG. 21 is a flowchart of a summary of an image processing method according to the third embodiment of the present invention.

FIG. 21 is a flowchart of a summary of a processing of an image processing method performed by the image processing apparatus 3. The summary of the processing of the image processing method according to the third embodiment will be explained below with reference to FIG. 21.

First, the image obtaining unit 101 obtains an image captured in an inside of a body cavity (a body cavity image) from the storage unit 31 similarly to the first embodiment (step S301).

After that, the resolution converter 309 creates a lower resolution image (an image whose resolution is lowered) with respect to the body cavity image (step S302). In the third embodiment, a resolution converting processing is repeatedly performed a predetermined number of times with respect to the image whose resolution is converted and images of plural kinds each having a different resolution are created. In other words, when the resolution does not reach a predetermined minimum resolution at step S303 ("No" at step S303), the processing at step S302 is repeatedly performed, and when the resolution reaches the predetermined minimum resolution ("Yes" at step S303), the pressing subsequently goes to step S304.

Figure 22:
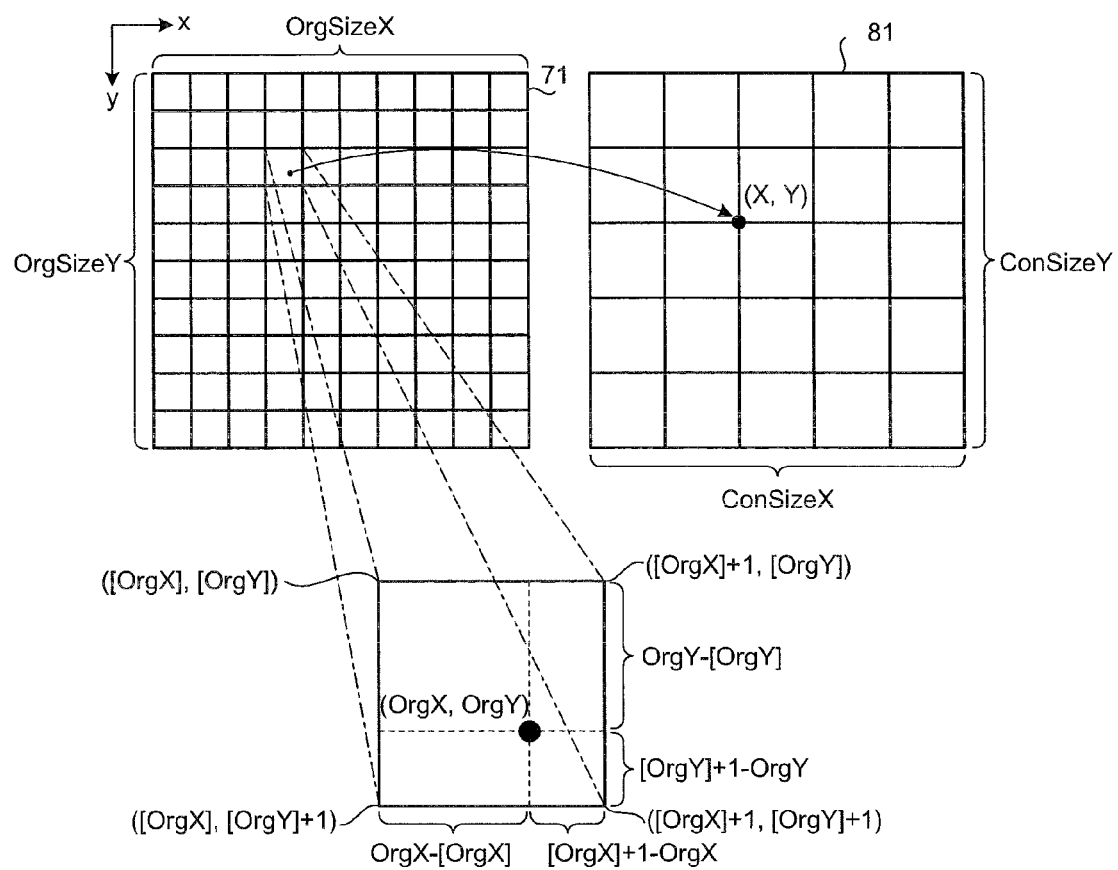
FIG. 22 schematically shows a pixel correspondence between an original image and an after-conversion image obtained via a resolution conversion.

For the resolution conversion performed by the resolution converter 309, any one of a wide variety of methods such as a bilinear interpolation, a nearest neighbor, and a bicubic interpolation can be applied. A case of performing the resolution conversion via the bilinear interpolation will be explained below with reference to FIG. 22. In the case shown in FIG. 22, a pixel which is standardized in a specified resolution is assumed to be present at a position of a grid point (an intersection point of a vertical line and a horizontal line) of an after-conversion image 81 whose resolution is already converted.

When an x-direction size of an original image 71 is OrgSizeX, a y-direction size is OrgSizeY, an x-direction size of the after-conversion image 81 is ConSizeX, and a y-direction size is ConSizeY, a zoom magnification $\omega_x$ in the x-direction of the image and a zoom magnification $\omega_y$ in the y-direction are expressed respectively by the following equations (24) and (25).

$$\omega_x = \frac{ConSizeX}{OrgSizeX} \quad (24)$$

$$\omega_y = \frac{ConSizeY}{OrgSizeY} \quad (25)$$

Elements OrgX and OrgY of a pixel(OrgX, OrgY), corresponding to a pixel(X,Y) of the after-conversion image, of the original image are expressed respectively by the following equations (26) and (27).

$$OrgX = \frac{X}{\omega_x} \quad (26)$$

$$OrgY = \frac{Y}{\omega_y} \quad (27)$$

Since the elements OrgX and OrgY calculated here are not necessarily integers, a corresponding pixel value cannot be obtained in the original image 71. Therefore, by using four pixels adjacent to the pixel(OrgX, OrgY) and taking a weighted average depending on a distance, a pixel value I(X, Y) of the pixel(X, Y) of the after-conversion image 81 is obtained in the bilinear interpolation. Specifically, when a pixel value at a pixel(x, y) of the original image 71 is set as an OrgI(x, y), the pixel value I(X, Y) of the pixel(X, Y) of the after-conversion image 81 is expressed by the following equation (28).

$$\begin{aligned}
I(X,Y) = &\,OrgI([OrgX],[OrgY]) \times ([OrgX]+1-OrgX) \times \\
&([OrgY]+1-OrgY) + OrgI([OrgX]+1,[OrgY]) \times \\
&(OrgX-[OrgX]) \times ([OrgY]+1-OrgY) + OrgI([OrgX], \\
&[OrgY]+1) \times ([OrgX]+1-OrgX) \times (OrgY-[OrgY]) + \\
&OrgI([OrgX]+1,[OrgY]+1) \times (OrgX-[OrgX]) \times \\
&(OrgY-[OrgY])
\end{aligned} \quad (28)$$

Here, "[ ]" is a gauss notation and represents a maximum integer value not exceeding a value in "[ ]".

Figure 23:
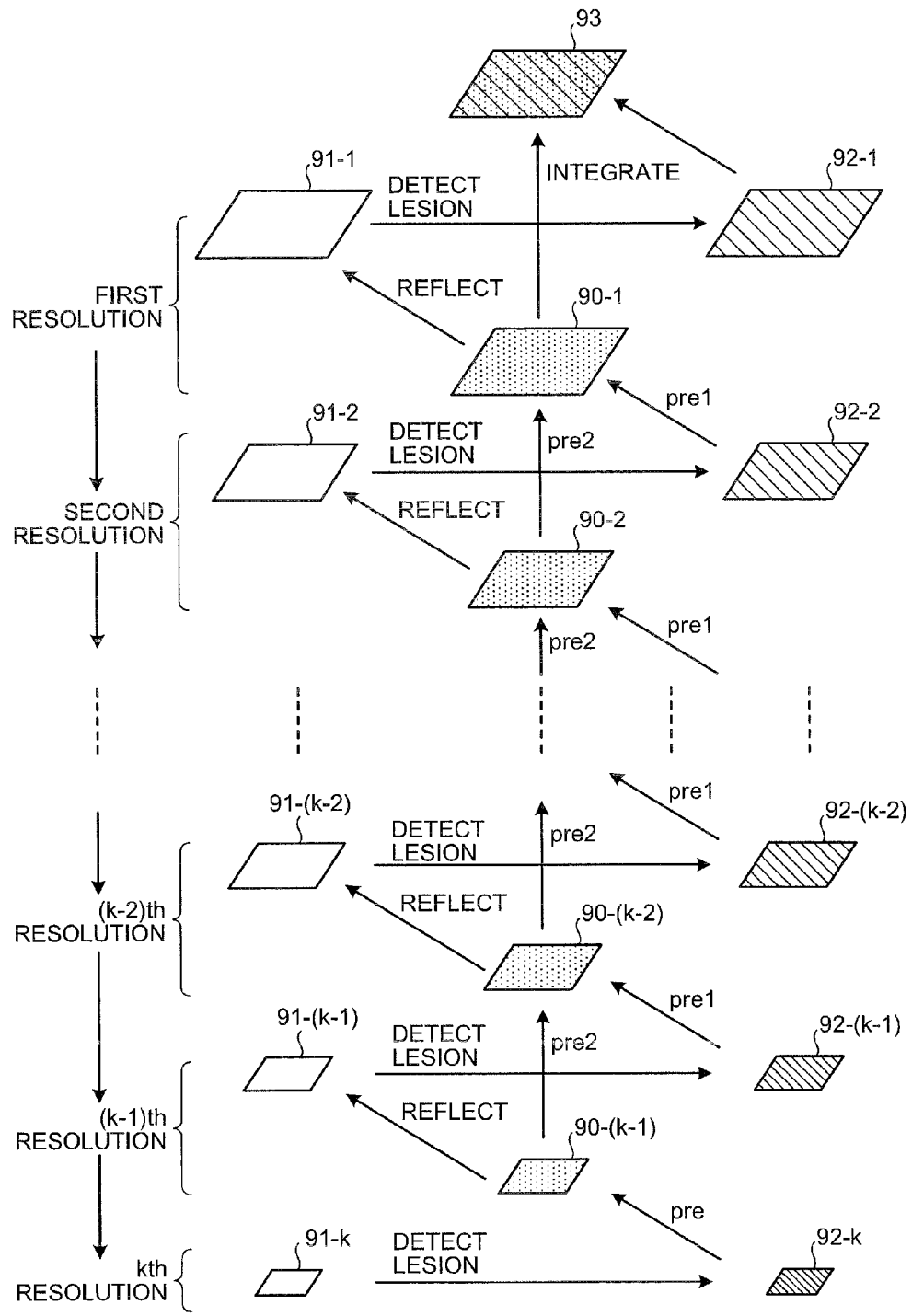
FIG. 23 shows a summary of a lesion detecting processing with respect to a multi-resolution image obtained via a resolution conversion.

FIG. 23 shows a summary of a processing after step S304, specifically showing a summary of a lesion detecting processing by using images of different resolutions. In FIG. 23, it is assumed that images of "k" kinds of resolutions ("k" is a positive integer) are created and a first resolution is a resolution of the original image. Besides, it is assumed that a second resolution is a lower resolution by one stage than the first resolution, a third resolution is a lower resolution by one stage than the second resolution, . . . , and a kth resolution is a lower resolution by one stage than a (k-1)th resolution. Therefore, the minimum resolution in this case is neither more nor less than the kth resolution.

First, the lesion detecting processing is performed with respect to a kth resolution image 91-*k* whose resolution is the lowest among unprocessed images (step S304). The lesion detecting processing at step S304 is the same as steps S202 to S217 shown in the second embodiment. An image obtained through a lesion detection in the kth resolution is treated as a kth-resolution lesion detection image 92-*k*.

Thereafter, the resolution converter 309 restores the kth-resolution lesion detection image 92-*k* to an image of (k-1)th resolution which is a higher resolution by one stage (one stage higher) than the kth-resolution lesion detection image 92-*k* (step S305), and the restored image is treated as a pre-(k-1)th-resolution lesion detection image 90-(*k*-1).

Next, a result of the lesion detection in the kth resolution is reflected to the (k-1)th-resolution image having a higher resolution by one stage than the kth-resolution image (step S306). Specifically, a (k-1)th-resolution image 91-(*k*-1) which is obtained by excluding, as a processing target, a pixel as a lesion in the pre-(k-1)th-resolution lesion detection image 90-(*k*-1) obtained at step S305 is created.

Here, when the resolution restored at step S305 (the (k-1)th resolution) is not the maximum resolution, i.e., the first resolution ("No" at step S307), the processing returns to step S304, and the lesion detecting processing (step S304) is performed with respect to the (k-1)th-resolution image 91-(*k*-1) whose resolution is the lowest among unprocessed images. An image as a result of the lesion detection in the (k-1)th resolution is treated as a (k-1)th-resolution lesion detection image 92-(*k*-1). In this manner, an image whose resolution is the lowest among images to which the lesion detecting processing is not performed (unprocessed images) generally becomes a processing target at step S304.

After that, the resolution converter 309 restores the result of the lesion detection in the (k-1)th resolution to an image of a (k-2)th resolution which is a higher resolution by one stage than the (k-1)th resolution (step S305). Specifically, the (k-1)th-resolution lesion detection image 92-(*k*-1) is restored to an image of the (k-2)th resolution which is a higher resolution by one stage than the (k-1) resolution, and treated as a pre1-(*k*-2)th-resolution lesion detection image. The pre-(k-1)th-resolution lesion detection image 90-(*k*-1) is also converted to an image of the (k-2)th resolution which is a higher resolution by one stage than the pre-(k-1)th resolution and treated as a pre2-(*k*-2)th-resolution lesion detection image. An image obtained by combining a pixel as a lesion in the pre1-(*k*-2)th-resolution lesion detection image with a pixel as a lesion in the pre2-(*k*-2)th-resolution lesion detection image is treated as a pre-(k-2)th-resolution lesion detection image 90-(*k*-2).

Next, the result of the lesion detection in the (k-1)th resolution is reflected to the (k-2)th-resolution image whose resolution is higher by one sage than the (k-1)th resolution (step S306). Specifically, a (k-2)th-resolution image 91-(*k*-2) which is obtained by excluding, as a processing target, a pixel as a lesion in the pre-(k-2)th-resolution lesion detection image 90-(*k*-2) is created.

After step S306, whether or not the resolution of the restored image (the (k-2)th resolution) is the maximum resolution is determined, the processing returns to step S304 when not the maximum resolution ("No" at step S307), and the processing at steps S304 to S307 is repeated with respect to the (k-2)th-resolution image 91-(*k*-2) whose resolution is the lowest among unprocessed images.

A processing to be performed subsequently when the resolution of the restored image is the maximum resolution, i.e., the resolution of the restored image is the first resolution ("Yes" at step S307) will be explained below. In this case, a lesion-detection integration image 93 in which a pixel as a lesion in the first-resolution lesion detection image 92-1 and a pixel as a lesion in the pre-first-resolution lesion detection image 90-1 are combined to be a pixel of a lesion is created (step S308). After that, the created lesion-detection integration image 93 is displayed on the display unit 107 as a lesion detection result (step S309). It is only necessary that this display is performed similarly to the display according to the first embodiment.

When a pixel which shows a change (concave/convex) in a pixel value with surroundings is extracted with respect to an image whose resolution is lowered via the resolution conversion, positions between a pixel of interest and surrounding pixels come to have relatively a long distance compared to positions in an image of an original resolution, so that a larger lesion region is extracted. In the third embodiment, a lesion is extracted in various sizes by preparing images of sequentially lowered plural resolutions and performing the lesion detecting processing with respect to each image. In the first and the second embodiments described above, a size of a lesion to be detected is specified by the number of pixels λ between the pixel of interest IP and the surrounding pixels $IA_{dir}$ and $IB_{dir}$ at the time of the calculation, performed by the change amount calculator 102, of a change (concave/convex) in a pixel value. In contrast, the third embodiment has a configuration which enables dealing with a detection of a lesion of various sizes.

According to the third embodiment described above, an image processing apparatus which can perform a high-speed lesion detecting processing to deal with various lesion sizes can be realized.

According to the present invention, an image processing apparatus, an image processing method, and an image processing program which are provided with a robustness against environmental differences in obtaining images and a high-speed performance that allows a processing of a large number of images for a short time, through a calculation of a pixel value change amount of a pixel of interest with a plurality of surrounding pixels located around the pixel of interest and an inter-surrounding-pixel change amount among the plurality of surrounding pixels with respect to a body cavity image captured in an inside of a living body, a detection of a candidate lesion region in the body cavity image based on results respectively obtained by a change amount calculator and an inter-surrounding-pixel change amount calculator, then an extraction of a feature of the detected candidate lesion region, and a detection of a lesion region from the candidate lesion region based on the extraction result.

According to the invention, an image processing apparatus provided with a robustness against environmental changes can be realized, not by using, as it is, color information of pixel values which tend to change easily due to a change in an imaging environment among different images, but by calculating a change amount with surrounding pixels in the same image, additionally calculating a bias between the surrounding pixels, treating a region which shows a pixel value change with the surroundings as a candidate lesion based on the bias of the surrounding pixels in addition to the pixel value change amount with the surroundings, and determining depending on a feature amount whether or not the region is a real lesion.

According to the invention, a lesion can be detected accurately and a high-speed processing can be realized by calculating a pixel value change amount of a pixel of a color component in which a pixel value change due to a lesion relatively tends to occur.

According to the invention, a lesion can be detected accurately and a high-speed processing can be realized by calculating a pixel value change amount in a G channel image in which a pixel value change due to a lesion relatively tends to occur.

According to the invention, compared to a case of calculating all pixels present around a pixel of interest, an increase of a calculation amount can be avoided by using surrounding pixels in a specified direction and calculating a pixel value change amount with the pixel of interest, and a calculation with a robustness against a pixel value change depending on a direction of an organ tissue or an incidental pixel value change is enabled by calculating a pixel value change amount for each direction.

According to the invention, since a region to be detected as a candidate lesion region is obtained depending on whether or not a pixel value change of the pixel of interest with the surrounding pixels is present, a size of a lesion to be extracted can be specified by a distance between the pixel of interest and the surrounding pixels.

According to the invention, not only an edge part having a steep pixel value change but also a change region itself due to a lesion can be extracted by treating pixels which are not adjacent to but away from the pixel of interest as the surrounding pixels.

According to the invention, when the pixel of interest is present at a margin of an image, a pixel value change amount of a pixel at a margin of the image with the surroundings can be calculated by setting appropriate surrounding pixels even in a case where any of the surrounding pixels gets out of the image.

According to the invention, a pixel of interest which shows a pixel value change with each of both surrounding pixels present opposite to each other across the pixel of interest can be extracted and an influence of a pixel value change due to a pixel value change gradient of an organ tissue itself can be reduced, via a weighting of the pixel value change amount calculated between the pixel of interest and the surrounding pixels by taking the bias in the pixel values of the surrounding pixels present opposite to each other across the pixel of interest as a center into consideration.

According to the invention, a pixel which is different from a peripheral tissue can be extracted as a pixel constituting a candidate lesion region by extracting a pixel of interest whose pixel value change amount calculated for each direction with the surroundings exceeds a predetermined range in all directions.

According to the invention, by recording a pixel value change amount which is obtained by organizing a weighted pixel value change amount calculated for each direction to a pixel extracted as a pixel value change pixel, the pixel value change amount can be used as a feature amount for a subsequent determination, performed by the lesion detector, of whether or not the region is a real lesion.

According to the invention, a feature amount which is effective in determining whether or not each region is a real lesion in the subsequent lesion detection is calculated in the candidate lesion region.

According to the invention, a lesion can be detected more accurately by eliminating a region not corresponding to a lesion from the candidate lesion region in advance.

According to the invention, a region to be detected as a lesion can be narrowed down by determining, after detecting a region in which a pixel value change with the surroundings is generated as a candidate lesion region, a region due to a shadow part, whose pixel value is changed not because of a lesion, of the organ wall groove.

According to the invention, by extracting a pixel which shows such a pixel value change as exceeding a predetermined threshold value in any one of the directions based on characteristics that a pixel value change at a groove part on the organ wall present a large change not in an extending direction of the organ wall but in a direction perpendicular to the extending direction of the organ wall, a region including a region corresponding to a groove region can be extracted and a groove region can be specified from the extracted region based on a region feature amount.

According to the invention, since a pixel value change region due to a non-lesion factor is also detected as a candidate lesion region, a candidate lesion region whose correspondence with a region corresponding to a groove in an expanded pixel value change region can be detected as a region generated at a shadow part of the organ wall groove by checking a correspondence between the candidate lesion region and the expanded pixel value change region.

According to the invention, since a food residue and an organ tissue are different substances and have a difference between their places in depth, a separation between a lesion and a non-lesion and an elimination are determined based on a fact that a pixel value change region generated by the food residue staying inside the body organ in the candidate lesion region presents a distribution different from a real lesion in an edge intensity at a contour part of the region.

According to the invention, a lesion detection accuracy can be improved and a high-speed processing can be realized by detecting, prior to a lesion detecting processing, a pixel which is, judging from a pixel value, clearly a pixel or a lesion to be a factor of a false detection in the lesion detecting processing.

According to the invention, since a pixel value change appears, when an extraneous noise is included in the body cavity image, from surroundings to the noise part and the part can be extracted as a candidate lesion region, a pixel affected by the noise is treated as a non-target pixel for the calculation by the change amount calculator and the inter-surrounding-pixel change amount calculator to suppress a false detection. Besides, a high-speed processing can be realized by specifying a pixel which is located at a dark part or develops a halation in luminance, and a part where a significant bleeding or a residue is concentrated over a wide range, and excluding the pixel or the part as a target for the pixel value change amount calculation using the pixel of interest and the surrounding pixels.

According to the invention, by taking it into a consideration that, though a change in a pixel value in each image is large due to differences in an imaging environment in the body cavity image, there is a difference seen in a distribution between a pixel value at a lesion part and a pixel value at a normal part in each image, a distribution of pixel values of a normal tissue in a corresponding image can be created by: treating a pixel which shows no pixel value change from a pixel value in the periphery of a pixel other than a non-target pixel having a noise and the like, and a pixel which belongs to a region that is regarded, despite showing a pixel value change from the pixel value in the periphery, by the groove detector as a groove region and that is in a predetermined non-lesion group determined by the non-lesion region determining unit; and setting these pixels as a normal pixel.

According to the invention, compared to a case of only performing a determination in a feature amount space based on master data obtained from a lot of sample images, a lesion region to be detected can be narrowed down by detecting a non-lesion region from the candidate lesion region based on the distribution of the pixel values of a normal tissue in the corresponding image.

According to the invention, since, by making an image resolution lower, positions, obtained by the change amount calculator and the inter-surrounding-pixel change amount calculator, between the pixel of interest and the surrounding pixels come to be relatively away compared to positions in an original image, a larger lesion can be detected. Furthermore, a detection of a lesion in various sizes can be realized by preparing images of various resolutions via the image resolution conversion and performing the lesion detection. In addition, repeating a resolution-lowering processing with respect to an image whose resolution is already lowered in creating various kinds of low-resolution images enables creating low-resolution images whose structure present in images is obscured in stages, so that an occurrence of a pixel not referred to in the original resolution image or an occurrence of a drastic change, involved in response to the occurrence of such a pixel, in a structure constituting the low-resolution image can be reduced compared to a case of directly creating an image whose resolution is fairly lower than the resolution of the original image.

According to the invention, a high-speed processing can be realized by performing a lesion detecting processing from an image of a minimum resolution in which the number of pixels constituting an image is small and by, while utilizing the detection result in the lesion detecting processing for an image of one-stage higher resolution, performing a lesion detection in images of sequentially higher resolutions.

According to the invention, a high-speed processing with a reduction in the number of pixels as a processing target can be realized by performing the lesion detecting processing from an image of a lower resolution and treating a pixel corresponding to a lesion region detected in the converted low-resolution image as a non-target pixel for the lesion detecting processing in an image of one-stage higher resolution.

According to the invention, whether or not a lesion is present, a position of the lesion, and what kind of lesion is present can be perceived quickly by allotting, for a display, a pixel value to a detected lesion depending on a kind of the lesion.

According to the invention, an image processing provided with a robustness against environmental changes can be realized, not by using, as it is, color information of pixel values which tend to change easily due to a change in an imaging environment among different images, but by calculating a change amount with surrounding pixels in the same image, additionally calculating a bias between surrounding pixels, treating a region which shows a pixel value change compared to the surroundings as a candidate lesion based on the bias of the surrounding pixels in addition to the pixel value change amount with the surroundings, and determining depending on a feature amount whether or not the region is a real lesion.

Though the present invention is explained above based on the embodiments, any combinations of the structural elements and processes and any equivalents obtained via a modification from the expressed invention into a computer program product and the like may also be valid as an aspect of the present invention. Here, the computer program product represents a material body to which the program is installed, such as a recording medium to which the program is recorded, and a stand-alone computer system and a network-type Internet system in which the program is read. In this case, the structural elements and processes described above are mounted in a module and the program-mounted module is incorporated in a computer program product.

In the embodiments described above, the candidate lesion region detector 104 detects a candidate lesion region in a body cavity image based on the pixel value change amount and the surrounding pixel value change amount. However, as a modification of the invention, the candidate lesion region detector 104 may detect a candidate lesion region based on the pixel value change amount without taking the surrounding pixel value change amount into consideration. In this case, instead of the surrounding pixel change amounts $B_{hor}$, $B_{ver}$, $B_{sla}$, and $B_{bac}$ obtained by equations (5) to (8), a constant "one", for example, may be assigned in equations (9) to (12) shown in the embodiments in the modification. This enables a detection of a candidate lesion region based on the pixel value change amount by leaving the surrounding pixel value change amount out of consideration. It should be noted that other processing except for the processing shown here is the same as that in the embodiments.

Though exemplary embodiments of the present invention are explained in detail so far as the first to the third embodiments, the present invention should not be limited only by the three embodiments described above. In other words, the present invention may comprehend various embodiments not set forth herein and various design modifications may be made without departing from the spirit or scope of the general inventive concept as defined by the appended claims and their equivalents.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing apparatus for performing an image processing on a body cavity image captured in a living body, comprising:
   a storage unit which stores information including image information of the body cavity image;
   a change amount calculator which reads out the image information of the body cavity image from the storage unit and calculates, in the read body cavity image, a pixel value change amount of a pixel of interest with a plurality of surrounding pixels located around the pixel of interest;
   a candidate lesion region detector which detects a candidate lesion region in the body cavity image based on a calculation result by the change amount calculator;
   an inter-surrounding-pixel change amount calculator which calculates a surrounding pixel value change amount between the plurality of surrounding pixels; and
   a non-target pixel determining unit which determines a non-target pixel to be excluded as one of a calculation target by the change amount calculator and a calculation target by the inter-surrounding-pixel change amount calculator.

2. The image processing apparatus according to claim 1, wherein the non-target pixel is an image noise pixel, a high luminance/low luminance pixel, a pixel constituting a food residue staining in an organ, and a pixel having a hue of a significant lesion origin.

3. The image processing apparatus according to claim 1, further comprising:
   a feature extracting unit which extracts a feature of the candidate lesion region detected by the candidate lesion region detector, and a lesion detector which detects a lesion region from the candidate lesion region based on a result extracted by the feature extracting unit, wherein the lesion detector includes:
- a normal-pixel-value-distribution creating unit which treats, among pixels except for the non-target pixel in the body cavity image, a value of a pixel in a region other than the candidate lesion region and a value of a pixel in a region belonging to a predetermined non-lesion group in the candidate lesion region as a pixel value of a normal organ tissue in a target image, and creates a normal pixel value distribution based on the pixel value of the normal organ tissue; and
- a normal-pixel-value-region eliminating unit which calculates a probability that each of the remaining candidate lesion regions is in the normal pixel value distribution, and eliminates a corresponding region from the candidate lesion region when the calculated probability is more than a predetermined threshold value.

4. The image processing apparatus according to claim 1, further comprising:
- a feature extracting unit which extracts a feature of the candidate lesion region detected by the candidate lesion region detector; and
- a lesion detector which detects a lesion region from the candidate lesion region based on a result extracted by the feature extracting unit, wherein the lesion detector includes an excessively-detected region eliminating unit which eliminates, from the candidate lesion region, one of a region that can be regarded as a structure of an organ inside a body and a region formed by a material different from a body organ tissue.

5. The image processing apparatus according to claim 4, wherein the excessively-detected region eliminating unit includes a groove eliminating unit which eliminates a shadow part caused by an organ wall groove from the candidate lesion region.

6. The image processing apparatus according to claim 5, wherein the groove eliminating unit includes:
- an expanded-pixel-value-change-region extracting unit which extracts the pixel of interest as an expanded pixel value change pixel when one of the pixel value change amount calculated by the change amount calculator for each direction and the weighted pixel value change amount calculated by the weighted change amount calculator for each direction exceeds a predetermined threshold value in anyone of the directions, performs a region division in which adjacent expanded pixel value change pixels are treated as a same region to extract as an expanded pixel value change region, and calculates a feature amount of the extracted expanded pixel value change region; and
- a groove region specifying unit which specifies a groove region based on the feature amount of the expanded pixel value change region calculated by the expanded-pixel-value-change-region extracting unit, the groove region specifying unit, by taking a correspondence between the candidate lesion region and the expanded pixel value change region into consideration, eliminating, as the shadow part of the organ wall groove the candidate lesion region corresponding to the expanded pixel value change region which is regarded as the groove region.

7. The image processing apparatus according to claim 4, wherein the excessively-detected region eliminating unit detects a region generated by a food residue staining in an organ inside a body in the candidate lesion region based on an edge intensity at a contour part of the region and eliminates the detected region from the candidate lesion region.

* * * * *